United States Patent
Riebel et al.

(10) Patent No.: US 6,440,903 B1
(45) Date of Patent: Aug. 27, 2002

(54) SUBSTITUTED 2,4-DIAMINO-1,3,5-TRIAZINES AS HERBICIDES

(75) Inventors: Hans-Jochem Riebel, Wuppertal; Stefan Lehr, Leverkusen; Uwe Stelzer, Burscheid, all of (DE); Yukiyoshi Watanabe, Oyama (JP); Markus Dollinger, Overland Park, KS (US); Seishi Ito, Oyama (JP); Toshio Goto, Kokubunji-machi (JP); Akihiko Yanagi, Oyama (JP)

(73) Assignees: Bayer Aktiengesellschaft, Leverkusen (DE); Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 09/269,820

(22) PCT Filed: Sep. 29, 1997

(86) PCT No.: PCT/EP97/05317

§ 371 (c)(1),
(2), (4) Date: Apr. 1, 1999

(87) PCT Pub. No.: WO98/15536

PCT Pub. Date: Apr. 16, 1998

(30) Foreign Application Priority Data

Oct. 10, 1996 (DE) .......................................... 196 41 692

(51) Int. Cl.$^7$ ...................... C07D 251/48; A01N 43/68
(52) U.S. Cl. ...................... 504/232; 504/233; 504/234; 544/206; 544/208
(58) Field of Search ................................ 544/206, 208; 504/232, 233, 234

(56) References Cited

U.S. PATENT DOCUMENTS

| | | | |
|---|---|---|---|
| 3,816,419 A | * 6/1974 | Cross et al. | 260/249.9 |
| 3,860,648 A | 1/1975 | Diamond et al. | 260/565 |
| 3,932,167 A | 1/1976 | Cross et al. | 71/93 |
| 3,970,700 A | 7/1976 | Nagase et al. | 260/570.8 R |
| 4,680,054 A | * 7/1987 | Takematsu et al. | 71/93 |
| 4,844,731 A | 7/1989 | Takematsu et al. | 71/93 |
| 4,874,420 A | * 10/1989 | Wroblowsky et al. | 71/93 |
| 5,144,077 A | 9/1992 | Jansen et al. | 564/438 |
| 5,183,939 A | 2/1993 | Jansen et al. | 564/302 |
| 5,290,754 A | 3/1994 | Nishii et al. | 504/232 |
| 5,300,437 A | 4/1994 | Stirling et al. | 435/280 |
| 5,739,328 A | 4/1998 | Schafer et al. | 544/194 |

FOREIGN PATENT DOCUMENTS

| | | | |
|---|---|---|---|
| DE | 3900300 | * | 7/1990 |
| EP | 0 411 153 | * | 2/1991 |

OTHER PUBLICATIONS

J. Am. Chem. Soc. (month unavailable) 1983, 105, pp. 1578–1584, Smith et al, Optically Active Amines. 31$^1$ Spectral Observations on the Substituted Benzene Chromophore $^2$.

Tetrahedron: Asymmetry, vol. 4, No. 9, pp. 2095–2100, (month unavailable) 1993, R. Sreekumar and C. LN. Pillai, Asymmetric Synthesis of Amines by the Reductive Amination of Ketones Unsing (+) and (–) Norephedrine Followed by Periodate Oxidation.

Chem. Abstracts, vol. 125, 58008z, Preparation of optically pure chiral amines by liphase–catalyzed enantioseletive hydrolysis of N–acyl–amines.

Biotechnology Techniques, vol. 10, May 1996, pp. 335–338, Sumidt et al, Preparation of Optically Pure Chiral Amines by Lipase–Catalyzed Enantioselective Hydrolysis of N–Acyl–Amines.

Chem Abstracts, vol. 109, 129062v, Preparation of triazine derivative as herbicides (1988).

Chemical Abstracts, vol. 109, No. 15, Oct. 10, 1988, Abstract No. 129062v, Takematsu, Tetsuo et al.: Preparation of triazine derivatives as herbicides XP002055062 & JP 62 294 669 A (Idemitsu Kosan Co., Ltd.).*

* cited by examiner

Primary Examiner—John M. Ford
(74) Attorney, Agent, or Firm—Joseph E. Gil; John E. Mrozinski, Jr.

(57) ABSTRACT

The invention relates to novel substituted 2,4-diamino-1,3,5-triazines of the formula (I)

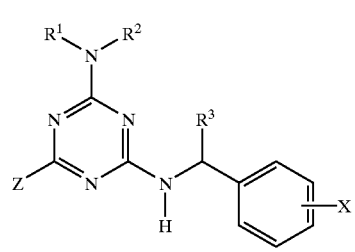

(I)

(in which $R^1$, $R^2$, $R^3$, X and Z are each as described in the description), to processes and to novel intermediates for their preparation and to their use as herbicides.

6 Claims, No Drawings

SUBSTITUTED 2,4-DIAMINO-1,3,5-TRIAZINES AS HERBICIDES

This is a 371 of PCT EP 97/05317, filed Sep. 29, 1997.

TECHNICAL FIELD OF THE INVENTION

The invention relates to novel substituted 2,4-diamino-1,3,5-triazines, to processes and to novel intermediates for their preparation and to their use as herbicides.

BACKGROUND OF THE INVENTION

A number of substituted 2,4-diamino-triazines is already known from the (patent) literature (cf U.S. Pat. No. 3,816,419, U.S. Pat. No. 3,932,167, EP 191496, EP 273328, EP 411153/WO 90/09378, JP 62294669—cited in Chem. Abstracts 109: 129062v). However, these compounds have hitherto not attained any particular importance.

DETAILED DESCRIPTION OF THE INVENTION

This invention, accordingly, provides the novel substituted 2,4-diamino-1,3,5-triazines of the general formula (I)

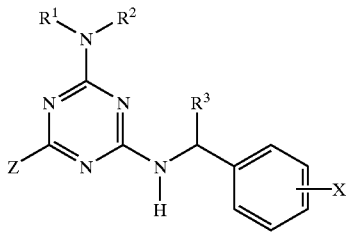

(I)

in which
- $R^1$ represents hydrogen or optionally hydroxyl-, cyano-, halogen- or $C_1$–$C_4$-alkoxy-substituted alkyl having 1 to 6 carbon atoms,
- $R^2$ represents hydrogen, represents formyl, represents in each case optionally cyano-, halogen- or $C_1$–$C_4$-alkoxy-substituted alkyl, alkylcarbonyl, alkoxycarbonyl or alkylsulphonyl having in each case 1 to 6 carbon atoms in the alkyl groups, or represents in each case optionally cyano-, halogen-, $C_1$–$C_4$-alkyl-, halogeno-$C_1$–$C_4$-alkyl-, $C_1$–$C_4$-alkoxy, halogeno-$C_1$–$C_4$-alkoxy- or $C_1$–$C_4$-alkoxy-carbonyl-substituted phenylcarbonyl, naphthylcarbonyl, phenylsulphonyl or napththylsulphonyl,
- $R^3$ represents optionally cyano-, halogen- or $C_{1-4}$-alkoxy-substituted alkyl having 1 to 6 carbon atoms or represents optionally cyano-, halogen- or $C_1$–$C_4$-alkyl-substituted cycloalkyl having 3 to 6 carbon atoms,
- X represents a substituent from the following group: hydroxyl, cyano, nitro, halogen, in each case optionally hydroxyl-, cyano- or halogen-substituted alkyl or alkoxy having in each case 1 to 6 carbon atoms, in each case optionally halogen-substituted alkylcarbonyl, alkoxycarbonyl, alkylthio, alkylsulphinyl or alkylsulphonyl having in each case 1 to 6 carbon atoms in the alkyl groups, in each case optionally hydroxyl-, cyano-, nitro-, halogen-, $C_1$–$C^4$-alkyl-, $C_1$–$C_4$-halogenoalkyl-, $C_1$–$C_4$-alkoxy- or $C_1$–$C_4$-halogenoalkoxy-substituted phenyl or phenoxy, and
- Z represents hydrogen, hydroxyl, halogen, represents in each case optionally hydroxyl-, cyano-, nitro-, halogen-, $C_1$–$C_4$-alkoxy-, $C_1$–$C_4$-alkyl-carbonyl-, $C_1$–$C_4$-alkoxy-carbonyl-, $C_1$–$C_4$-alkylthio-, $C_1$–$C_4$-alkylsulphinyl- or $C_1$–$C_4$-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups, represents in each case optionally halogen-substituted alkenyl or alkinyl having in each case 2 to 6 carbon atoms, or represents optionally cyano-, halogen- or $C_1$–$C_4$-alkyl-substituted cycloalkyl having 3 to 6 carbon atoms, but excluding the compounds
2-amino- 4-methoxy-6-[1-(3-chlorophenyl)-ethylamino]-1,3,5-triazine, 2-amino-4-methoxy-6-[1-(3-methyl-phenyl)-ethylamino]-1,3,5-triazine, 2-amino-4-chloro-6-[1-(3-trifluoromethyl-phenyl)-ethylamino]-1,3,5-triazine, 2-amino-4-chloro-6-[1-(3-nitrophenyl)-ethylamino-1,3,5-triazine, 2-amino-4-chloro-6-[1-(3-chloro-phenyl)-ethylamino]- 1,3,5-triazine and 2-amino-4-chloro-6-[1-(3-methyl-phenyl)-ethylamino]-1,3,5-triazine
(which are already known from JP 62294669).

The novel 2,4-diamino-1,3,5-triazines of the general formula (I) are obtained when (a) substituted biguanides of the general formula (II),

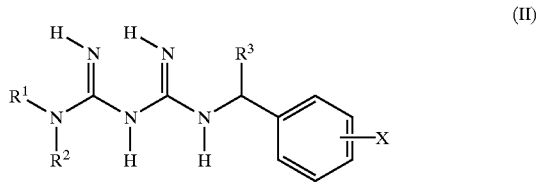

(II)

in which
$R^1$, $R^2$, $R^3$ and X are each as defined above
and/or acid adducts of compounds of the general formula (II)
are reacted with alkoxycarbonyl compounds of the general formula (III)

Z—CO—OR'  (III)

in which
Z is as defined above and
R' represents alkyl,
if appropriate in the presence of a reaction auxiliary and if appropriate in the presence of a diluent,
or when (b) substituted aminotriazines of the general formula (IV)

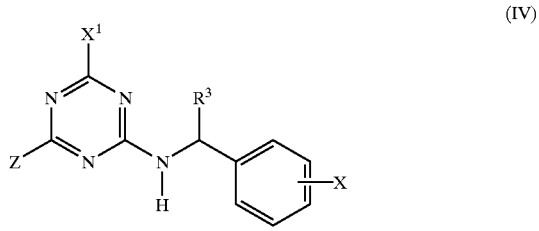

(IV)

in which
$R^3$, X and Z are each as defined above and
$X^1$ represents halogen or alkoxy
are reacted with nitrogen compounds of the general formula (V)

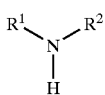
(V)

in which
R¹ and R² are each as defined above,
if appropriate in the presence of a reaction auxiliary and if appropriate in the presence of a diluent,
or when (c) substituted aminotriazines of the general formula (VI),

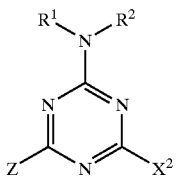
(VI)

in which
R¹, R² and Z are each as defined above and
X² represents halogen or alkoxy
are reacted with amino compounds of the general formula (VII),

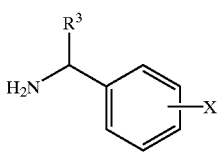
(VII)

in which
R³ and X are each as defined above,
if appropriate in the presence of a reaction auxiliary and if appropriate in the presence of a diluent,
or when (d) to prepare compounds of the formula (I), except for those where R²=H, 2,4-diamino-1,3,5-triazines of the general formula (Ia)

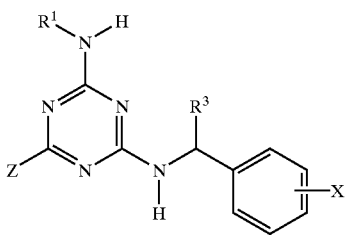
(Ia)

in which
R¹, R³, X and Z are each as defined above
are reacted with alkylating, acylating or sulphonylating agents of the general formula (VIII)

Y—R²   (VIII)

in which
R² is as defined above—except for hydrogen—and
Y represents halogen, alkoxy, alkoxysulphonyloxy or acyloxy, if appropriate in the presence of a reaction auxiliary and if appropriate in the presence of a diluent,
and, if appropriate, further conversions within the scope of the above definition of substituents are carried out by customary methods on the compounds of the general formula (I) obtained by the processes described under (a), (b), (c) or (d).

The novel substituted 2,4-diamino-1,3,5-triazines of the general formula (I) have strong and selective herbicidal activity.

The compounds of the general formula (I) according to the invention contain at least one asymmetrically substituted carbon atom and can therefore be present in different enantiomeric (R- and S-configured forms) or diastereomeric forms. The invention relates both to the different possible individual enantiomeric or stereoisomeric forms of the compounds of the general formula (I), and to the mixtures of these isomeric compounds.

In the definitions, the hydrocarbon chains, such as alkyl—also in combination with heteroatoms, such as in alkoxy or alkylthio—are in each case straight-chain or branched.

Halogen generally represents fluorine, chlorine, bromine or iodine, preferably represents fluorine, chlorine or bromine, and in particular represents fluorine or chlorine.

The invention preferably provides compounds of the formula (I) in which

R¹ represents hydrogen or represents optionally hydroxyl-, cyano-, fluorine-, chlorine-, methoxy- or ethoxy-substituted alkyl having 1 to 4 carbon atoms, R² represents hydrogen, represents formyl, represents in each case optionally cyano-, fluorine-, chlorine-, methoxy- or ethoxy-substituted alkyl, alkylcarbonyl, alkoxycarbonyl or alkylsulphonyl having in each case 1 to 4 carbon atoms in the alkyl groups, or represents in each case optionally cyano-, fluorine-, chlorine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methoxycarbonyl- or ethoxycarbonyl-substituted phenylcarbonyl or phenylsulphonyl, R³ represents optionally hydroxyl-, cyano-, fluorine-, chlorine-, methoxy- or ethoxy-substituted alkyl having 1 to 4 carbon atoms or represents optionally cyano-, fluorine-, chlorine-, methyl- or ethyl-substituted cycloalkyl having 3 to 6 carbon atoms, x represents a substituent from the group below:
hydroxyl, cyano, nitro, fluorine, chlorine, bromine, iodine, in each case optionally hydroxyl-, cyano-, fluorine- or chlorine-substituted alkyl or alkoxy having in each case 1 to 4 carbon atoms, in each case optionally fluorine- or chlorine-substituted alkylcarbonyl, alkoxycarbonyl, alkylthio, alkylsulphinyl or alkylsulphonyl having in each case 1 to 4 carbon atoms in the alkyl groups, in each case optionally hydroxyl-, cyano-, nitro-, fluorine-, chlorine-, bromine-, iodine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy, and Z represents hydrogen, hydroxyl, fluorine, chlorine, bromine, represents in each case optionally hydroxyl-, cyano-, nitro-, fluorine-, chlorine-, methoxy-, ethoxy-, acetyl-, propionyl-, methoxycarbonyl-, ethoxycarbonyl-, methylthio-, ethylthio-, methylsulphinyl-, ethylsulphinyl-, methylsulphonyl- or ethylsulphonyl-substituted alkyl, alkoxy, alkylcarbonyl, alkoxycarbonyl, alkylthio, alkylsulphinyl or alkylsulphonyl having in each case 1 to 4 carbon atoms in the alkyl groups, represents in each case optionally fluorine-, chlorine- or bromine-substituted alkenyl or alkinyl having in each case 2 to 4 carbon atoms, or represents optionally cyano-, fluorine-, chlorine-, methyl- or ethyl-substituted cycloalkyl having 3 to 6 carbon atoms, but excluding the compounds
2-amino-4-methoxy-6-[1-(3-chlorophenyl)-ethylamino]-1,3,5-triazine, 2-amino-4-methoxy-6-[1-(3-methyl-phenyl)-ethylamino]-1,3,5-triazine, 2-amino-4-chloro-6-[1-(3-trifluoromethyl-phenyl)-ethylamino]-1,3,5-triazine, 2-amino-4-chloro-6-[1-(3-nitrophenyl)-ethylamino]-1,3,5-triazine, 2-amino-4-chloro-6-[1-(3-chloro-phenyl)-ethylamino]-1,3,5-triazine and 2-amino-4-chloro-6-[1-(3-methyl-phenyl)-ethylamino]-1,3,5-triazine (which are already known from JP 62294669).

The invention in particular relates to compounds of the formula (I) in which $R^1$ represents hydrogen or represents optionally hydroxyl-, cyano-, fluorine-, chlorine-, methoxy- or ethoxy-substituted methyl, ethyl, n- or i-propyl, $R^2$ represents hydrogen, represents formyl, represents in each case optionally cyano-, fluorine-, chlorine-, methoxy- or ethoxy-substituted methyl, ethyl, acetyl, propionyl, methoxycarbonyl, ethoxycarbonyl, methylsulphonyl or ethylsulphonyl, or represents in each case optionally cyano-, fluorine-, chlorine-, methyl-, ethyl-, trifluoromethyl-, methoxy-, ethoxy-, difluoromethoxy-, trifluoromethoxy-, methoxycarbonyl- or ethoxycarbonyl-substituted phenylcarbonyl or phenylsulphonyl, $R^3$ represents in each case optionally hydroxyl-, cyano-, fluorine-, chlorine-, methoxy- or ethoxy-substituted methyl, ethyl, n- or i-propyl, or represents in each case optionally cyano-, fluorine-, chlorine-, methyl- or ethyl-substituted cyclopropyl, cyclobutyl, cyclopentyl or cyclohexyl, X represents a substituent from the group below:
hydroxyl, cyano, nitro, fluorine, chlorine, bromine, in each case optionally hydroxyl-, cyano-, fluorine- or chlorine-substituted methyl, ethyl, n- or i-propyl, n-, i-, s- or t-butyl, methoxy, ethoxy, n- or i-propoxy, in each case optionally fluorine- or chlorine-substituted acetyl, propionyl, methoxycarbonyl, ethoxycarbonyl, methylthio, ethylthio, methylsulphinyl, ethylsulphinyl, methylsulphonyl or ethylsulphonyl, in each case optionally hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy or trifluoromethoxy-substituted phenyl or phenoxy, and Z represents hydrogen, hydroxyl, fluorine, chlorine, bromine, represents in each case optionally hydroxyl-, cyano-, nitro-, fluorine-, chlorine-, methoxy-, ethoxy-, acetyl-, propionyl-, methoxycarbonyl-, ethoxycarbonyl-, methylthio-, ethylthio-, methylsulphinyl-, ethylsulphinyl-, methylsulphonyl- or ethylsulphonyl-substituted methyl, ethyl, n- or i-propyl, methoxy, ethoxy, n- or i-propoxy, acetyl, propionyl, methoxycarbonyl,ethoxycarbonyl, methylthio, ethylthio, methylsulphinyl, ethylsulphinyl, methylsulphonyl or ethylsulphonyl, or represents in each case optionally fluorine-, chlorine- or bromine-substituted ethenyl, propenyl, butenyl, ethinyl, propinyl or butinyl, but excluding the compounds
2-amino-4-methoxy-6-[1-(3-chlorophenyl)-ethylamino]-1,3,5-triazine, 2-amino-4-methoxy-6-[1-(3-methyl-phenyl)-ethylamino]-1,3,5-triazine, 2-amino-4-chloro-6-[1-(3-trifluoromethyl-phenyl)-ethylamino]-1,3,5-triazine, 2-amino-4-chloro-6-[1-(3-nitrophenyl)-ethylamino]-1,3,5-triazine, 2-amino-4-chloro-6-[1-(3-chloro-phenyl)-ethylamino]-1,3,5-triazine and 2-amino4-chloro-6-[1-(3-methyl-phenyl)-ethylamino]-1,3,5-triazine (which are already known from JP 62294669).

The abovementioned general or preferred radical definitions apply both to the end products of the formula (I) and also, correspondingly, to the starting materials or intermediates required in each case for the preparation. These radical definitions can be combined with each other at will, i.e. including combinations between the abovementioned preferred ranges.

Examples of the compounds of the formula (I) according to the invention are listed in the groups below. The general formulae here represent in each case the R enantiomers, the S enantiomers and the racemates.

Group 1

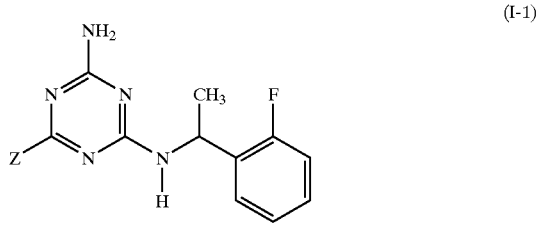

(I-1)

Here, Z has, for example, the meanings given below:

Hydrogen, methyl, ethyl, n- or i-propyl, n-, i-, s- or t-butyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloro-ethyl, 1-chloro-1-fluoro-ethyl, 1-fluoro-propyl, 2-fluoro-propyl, 3-fluoro-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-chloro-1-ethyl-propyl, 1-fluoro-2-methyl-propyl, 1-chloro-2-methyl-propyl, 1-chloro-propyl, 2-chloro-propyl, 3-chloro-propyl, 1-chloro-1-methyl-ethyl, 2-chloro-1-methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluoropentyl, perfluorohexyl, 1-hydroxyl-ethyl, acetyl, 1,1-bis-acetyl-methyl, 1-acetyl-1-methoxycarbonyl-methyl, 1-acetyl-1-ethoxycarbonyl-methyl, methoxymethyl, 1,1-dimethoxy-methyl, 1-methoxy-ethyl, 2-methoxy-ethyl, 1,1-dimethoxy-ethyl, ethoxymethyl, 1-ethoxyethyl, 2-ethoxyethyl, 2-methoxy-1-methyl-ethyl, 2-methoxy-1-ethyl-ethyl, 2-ethoxy-1-methyl-ethyl, 2-ethoxy-1-ethyl-ethyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl, methoxy, ethoxy, n- or i- propoxy, methylthio, ethylthio, n- or i-propylthio, methylsulphinyl, ethylsulphinyl, methylsulphonyl, ethylsulphonyl, fluoromethoxy, difluoromethoxy, trifluoromethoxy, fluoroethoxy, difluoroethoxy, trifluoroethoxy, difluoromethylthio, trifluoromethylthio, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 2-bromo-2-chloro-vinyl, trichlorovinyl, allyl, 2-chloro-allyl, 3-chloro-allyl, 3,3-dichloro-allyl, 1-propenyl, isopropenyl, 1-chloro-2-propenyl, 1-fluoro-2-propenyl, 1-bromo-2-propenyl, 1,2-dichloro-1-propenyl, 1,2-dibromo-1-propenyl, 1,2-difluoro-1-propenyl, 1,1-dichloro-2-propenyl, 1,1-dibromo-2-propenyl, 1,1-difluoro-2-propenyl, 1,1,3,3,3-pentafluoro-2-propenyl, 2-buten-1-yl, 2-buten-2-yl, 3-chloro-2-butenyl, 3-bromo-2-butenyl, 3,3,3-trifluoro-2-butenyl, ethinyl, 2-chloro-ethinyl, 2-bromo-ethinyl, 1-propinyl, 2-propinyl, 3,3,3-trifluoro-1-propinyl.

Group 2

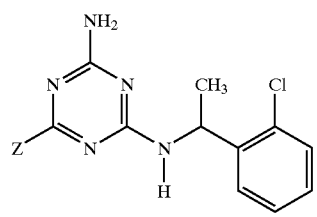

(I-2)

Here, Z has, for example, the meanings given above in group 1.

Group 3

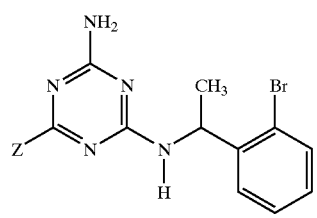

(I-3)

Here, Z has, for example, the meanings given above in group 1.

Group, 4

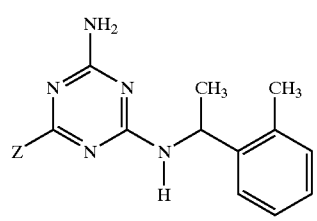

(I-4)

Here, Z has, for example, the meanings given above in group 1.

Group 5

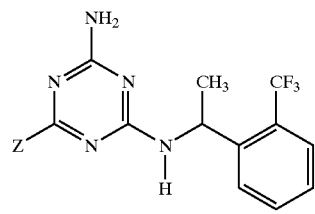

(I-5)

Here, Z has, for example, the meanings given above in group 1.

Group 6

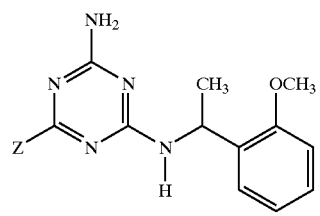

(I-6)

Here, Z has, for example, the meanings given above in group 1.

Group 7

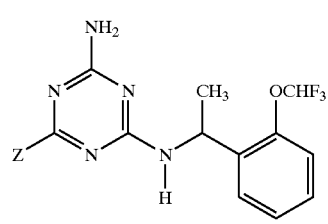

(I-7)

Here, Z has, for example, the meanings given above in group 1.

Group 8

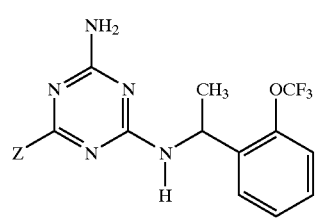

(I-8)

Here, Z has, for example, the meanings given above in group 1.

Group 9

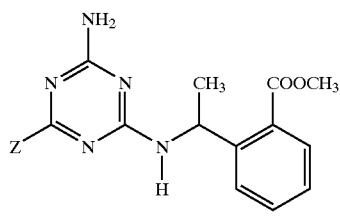
(I-9)

Here, Z has, for example, the meanings given above in group 1.

Group 10

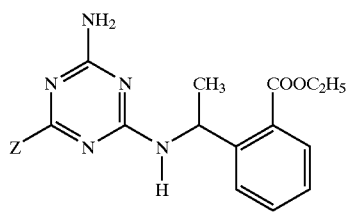
(I-10)

Here, Z has, for example, the meanings given above in group 1.

Group 11

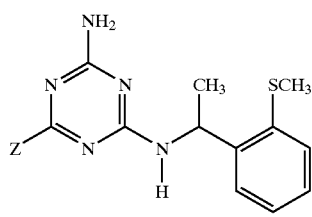
(I-11)

Here, Z has, for example, the meanings given above in group 1.

Group 12

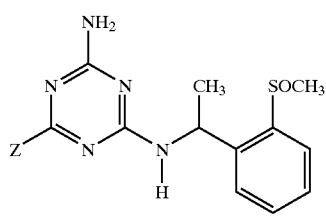
(I-12)

Here, Z has, for example, the meanings given above in group 1.

Group 13

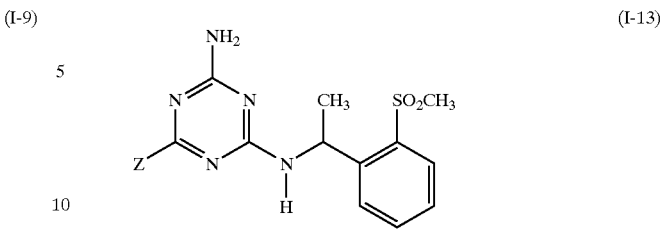
(I-13)

Here, Z has, for example, the meanings given above in group 1.

Group 14

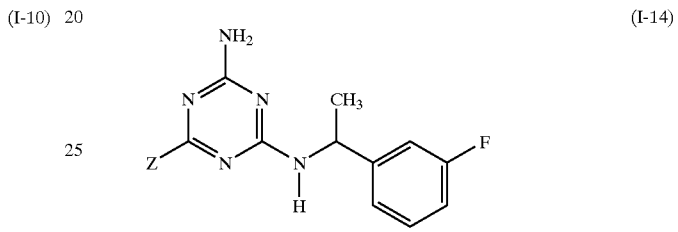
(I-14)

Here, Z has, for example, the meanings given above in group 1.

Group 15

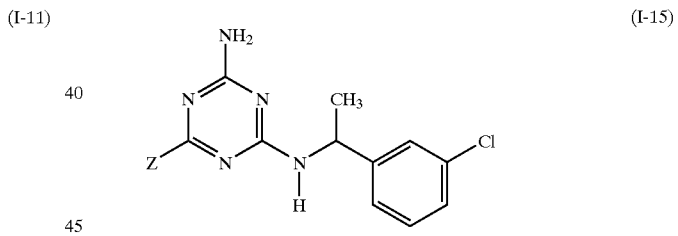
(I-15)

Here, Z has, for example, the meanings given above in group 1.

Group 16

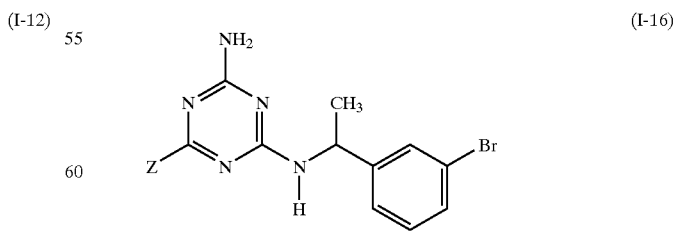
(I-16)

Here, Z has, for example, the meanings given above in group 1.

Group 17

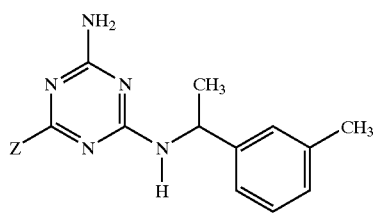
(I-17)

Here Z has, for example, the meanings given above in group 1.

Group 18

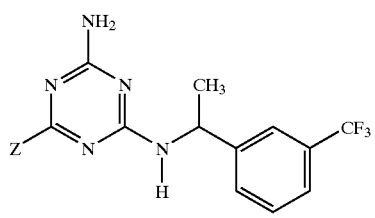
(I-18)

Here, Z has, for example, the meanings given above in group 1.

Group 19

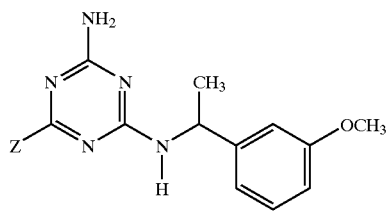
(I-19)

Here, Z has, for example, the meanings given above in group 1.

Group 20

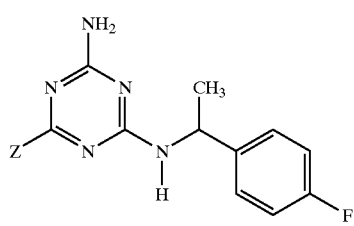
(I-20)

Here, Z has, for example, the meanings given above in group 1.

Group 21

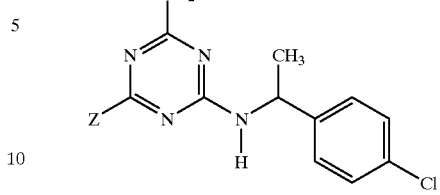
(I-21)

Here, Z has, for example, the meanings given above in group 1.

Group 22

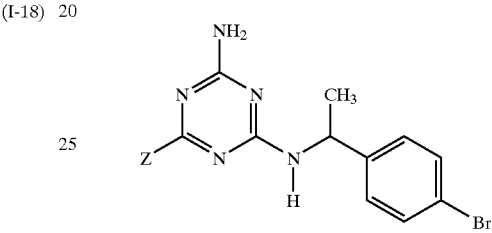
(I-22)

Here, Z has, for example, the meanings given above in group 1.

Group 23

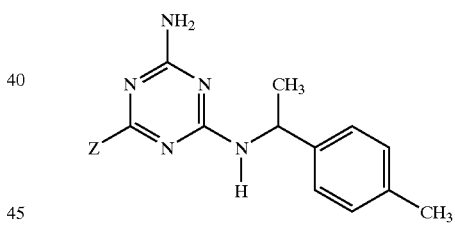
(I-23)

Here, Z has, for example, the meanings given above in group 1.

Group 24

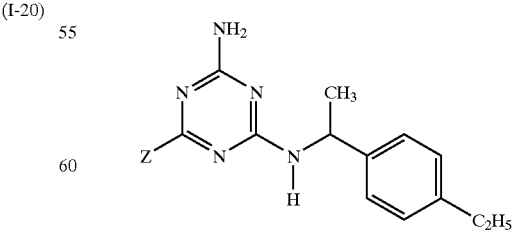
(I-24)

Here, Z has, for example, the meanings given above in group 1.

Group 25

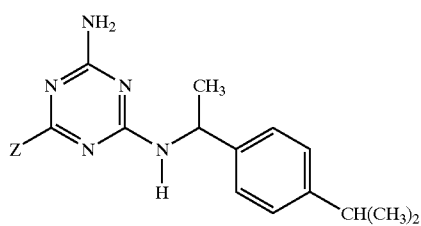
(I-25)

Here, Z has, for example, the meanings given above in group 1.

Group 26

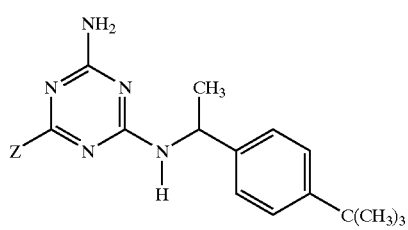
(I-26)

Here, Z has, for example, the meanings given above in group 1.

Group 27

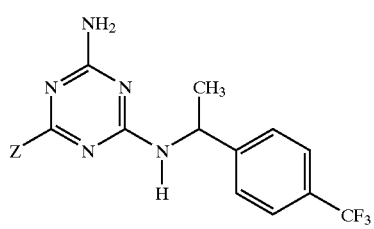
(I-27)

Here, Z has, for example, the meanings given above in group 1.

Group 28

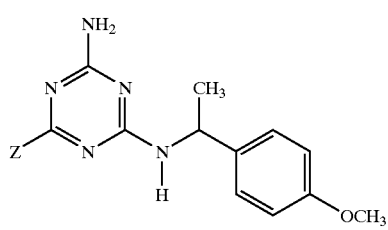
(I-28)

Here, Z has, for example, the meanings given above in group 1.

Group 29

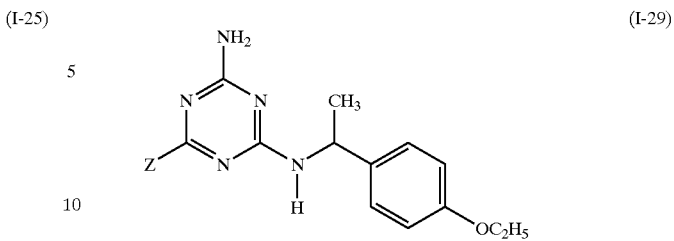
(I-29)

Here, Z has, for example, the meanings given above in group 1.

Group 30

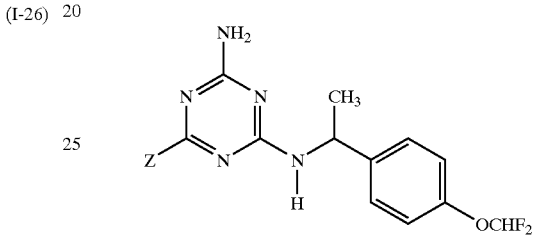
(I-30)

Here, Z has, for example, the meanings given above in group 1.

Group 31

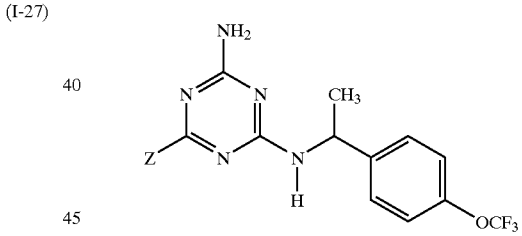
(I-31)

Here, Z has, for example, the meanings given above in group 1.

Group 32

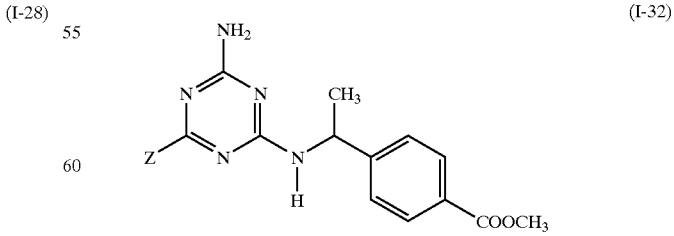
(I-32)

Here, Z has, for example, the meanings given above in group 1.

Group 33

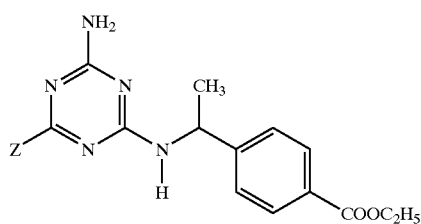
(I-33)

Here, Z has, for example, the meanings given above in group 1.

Group 34

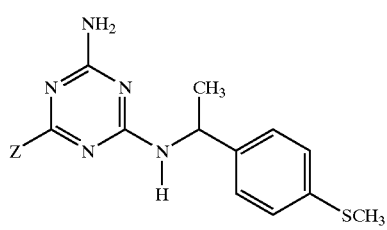
(I-34)

Here, Z has, for example, the meanings given above in group 1.

Group 35

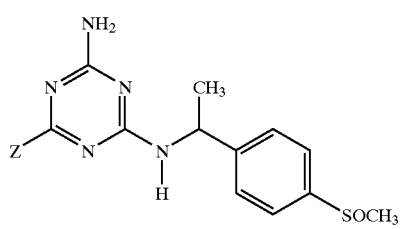
(I-35)

Here, Z has, for example, the meanings given above in group 1.

Group 36

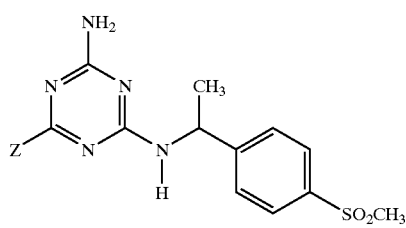
(I-36)

Here, Z has, for example, the meanings given above in group 1.

Group 37

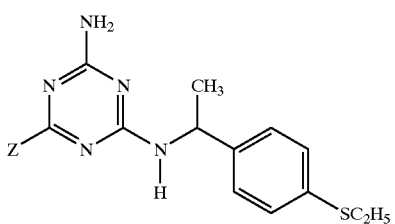
(I-37)

Here, Z has, for example, the meanings given above in group 1.

Group 38

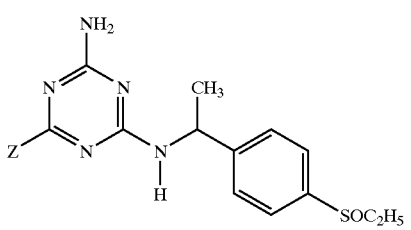
(I-38)

Here, Z has, for example, the meanings given above in group 1.

Group 39

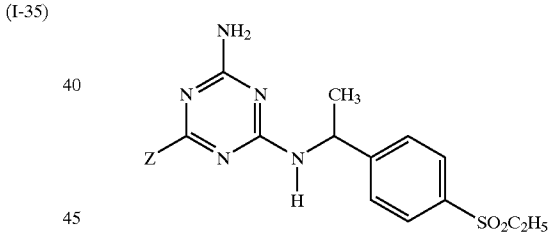
(I-39)

Here, Z has, for example, the meanings given above in group 1.

Group 40

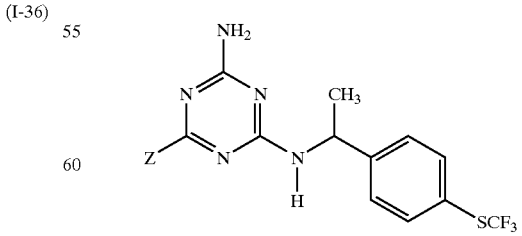
(I-40)

Here, Z has, for example, the meanings given above in group 1.

Group 41

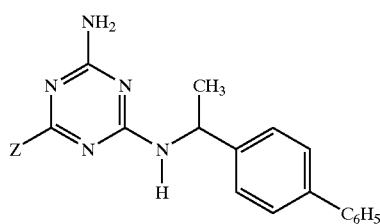
(I-41)

Here, Z has, for example, the meanings given above in group 1.

Group 42

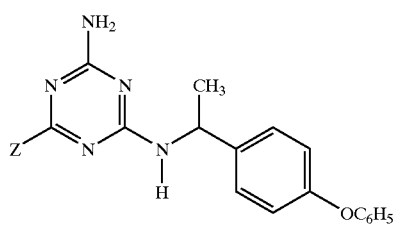
(I-42)

Here, Z has, for example, the meanings given above in group 1.

Group 43

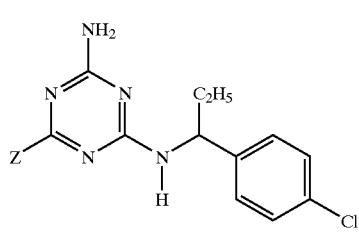
(I-43)

Here, Z has, for example, the meanings given above in group 1.

Group 44

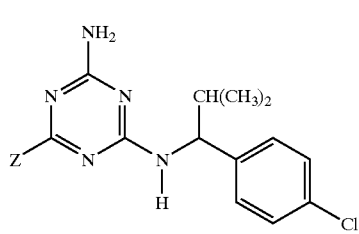
(I-44)

Here, Z has, for example, the meanings given above in group 1.

Group 45

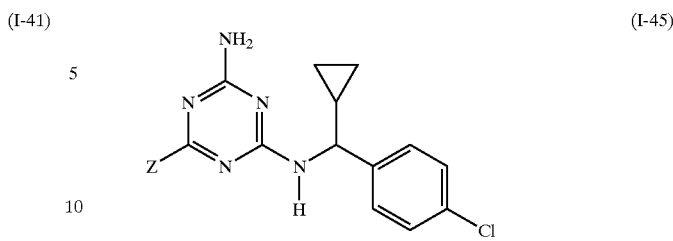
(I-45)

Here, Z has, for example, the meanings given above in group 1.

Group 46

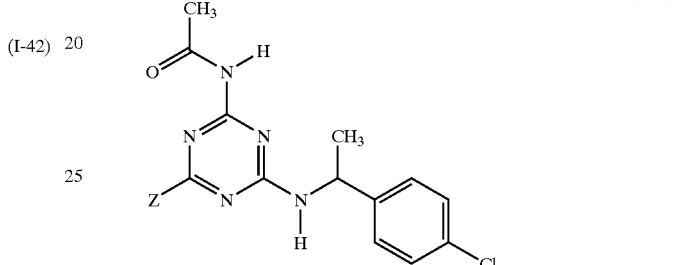
(I-46)

Here, Z has, for example, the meanings given above in group 1.

Group 47

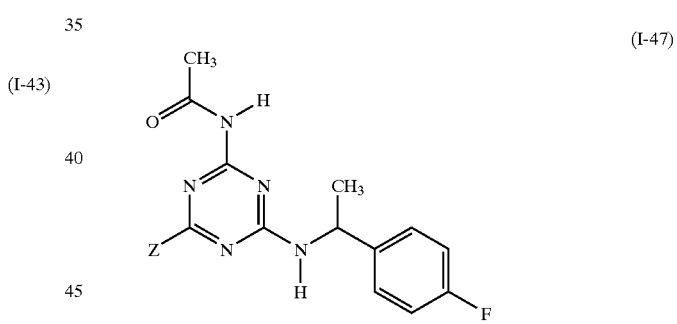
(I-47)

Here, Z has, for example, the meanings given above in group 1.

Group 48

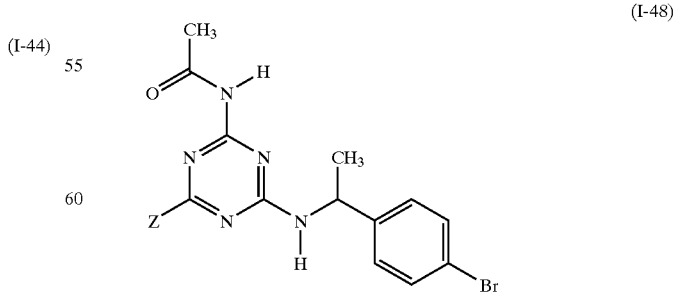
(I-48)

Here, Z has, for example, the meanings given above in group 1.

Group 49

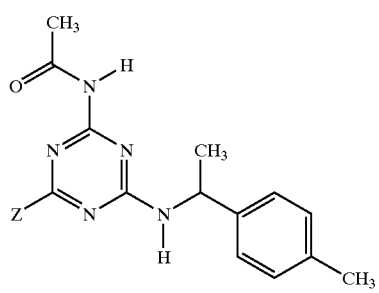
(I-49)

Here, Z has, for example, the meanings given above in group 1.

Group 50

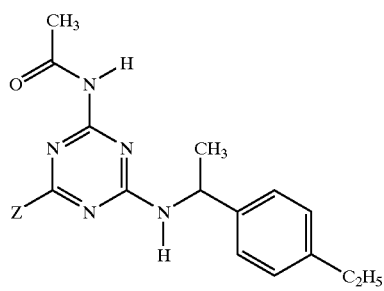
(I-50)

Here, Z has, for example, the meanings given above in group 1.

Group 51

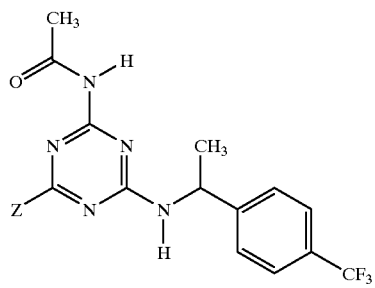
(I-51)

Here, Z has, for example, the meanings given above in group 1.

Group 52

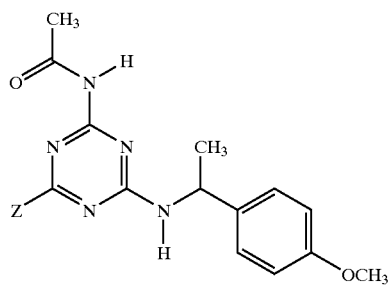
(I-52)

Here, Z has, for example, the meanings given above in group 1.

Group 53

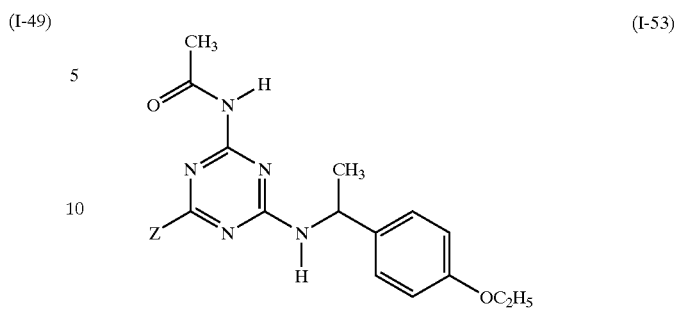
(I-53)

Here, Z has, for example, the meanings given above in group 1.

Group 54

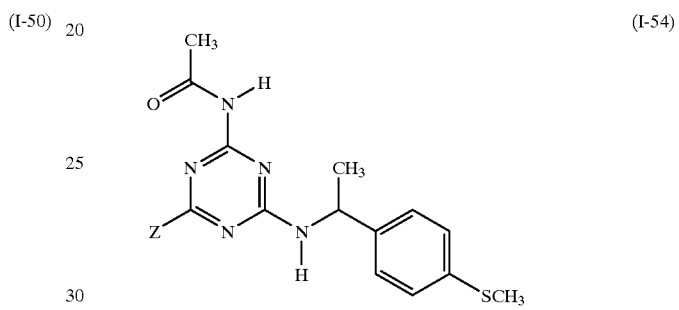
(I-54)

Here, Z has, for example, the meanings given above in group 1.

Group 55

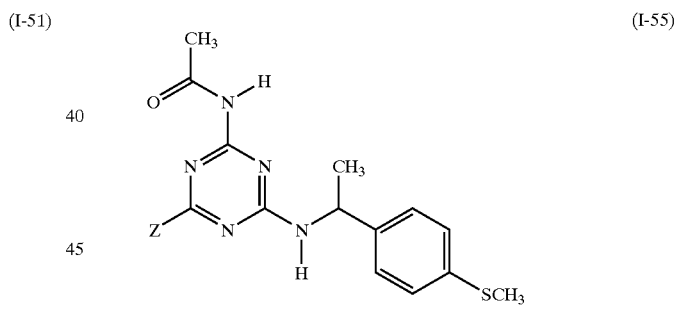
(I-55)

Here, Z has, for example, the meanings given above in group 1.

Group 56

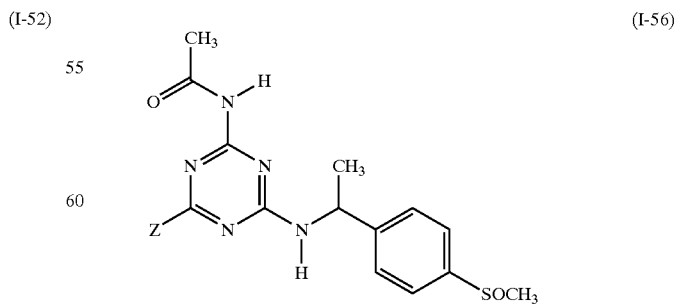
(I-56)

Here, Z has, for example, the meanings given above in group 1.

Group 57

(I-57)

[Structure I-57]

Here, Z has, for example, the meanings given above in group 1.

Group 58

(I-58)

[Structure I-58]

Here, Z has, for example, the meanings given above in group 1.

Group 59

(I-59)

[Structure I-59]

Here, Z has, for example, the meanings given above in group 1.

Group 60

(I-60)

[Structure I-60]

Here, Z has, for example, the meanings given above in group 1.

Group 61

(I-61)

[Structure I-61]

Here, Z has, for example, the meanings given above in group 1.

Group 62

(I-62)

[Structure I-62]

Here, Z has, for example, the meanings given above in group 1.

Group 63

(I-63)

[Structure I-63]

Here, Z has, for example, the meanings given above in group 1.

Group 64

(I-64)

[Structure I-64]

Here, Z has, for example, the meanings given above in group 1.

Group 65

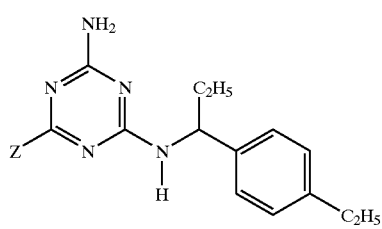
(I-65)

Here, Z has, for example, the meanings given above in group 1.

Group 66

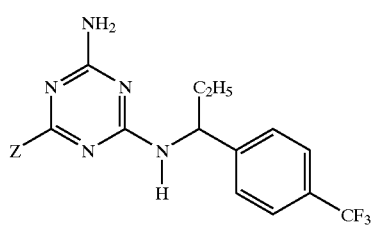
(I-66)

Here, Z has, for example, the meanings given above in group 1.

Using, for example, 1-[1-(4-chloro-phenyl)-ethyl] biguanide and methyl trifluoroacetate as starting materials, the course of the reaction in the process (a) according to the invention can be illustrated by the following equation:

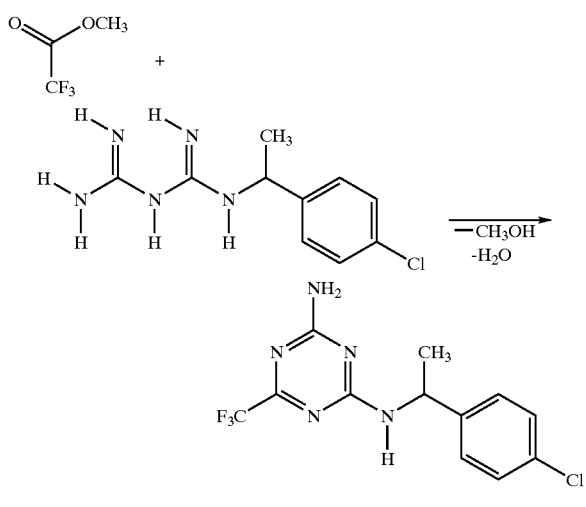

Using, for example, 2-chloro- 4[1-(3-fluoro-phenyl)-propylamino]-6-(1-chloro-ethyl)-1,3,5-triazine and ammonia as starting materials, the course of the reaction in the process (b) according to the invention can be illustrated by the following equation:

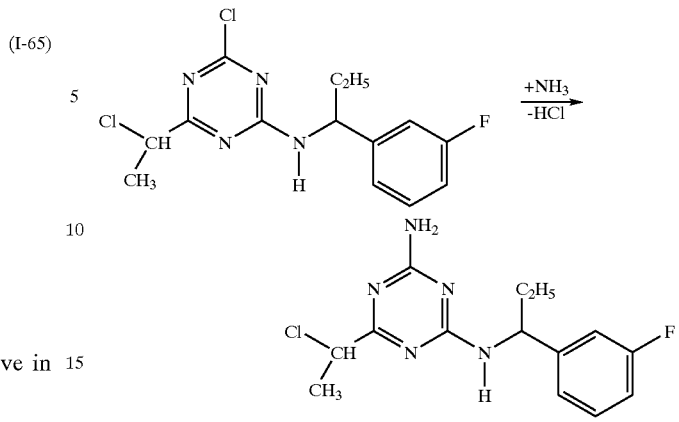

Using, for example, 2-amino-4-methoxy-6-trifluoromethyl-1,3,5-triazine and 1-(4-ethyl-phenyl)-propylamine as starting materials, the course of the reaction in the process (c) according to the invention can be illustrated by the following equation:

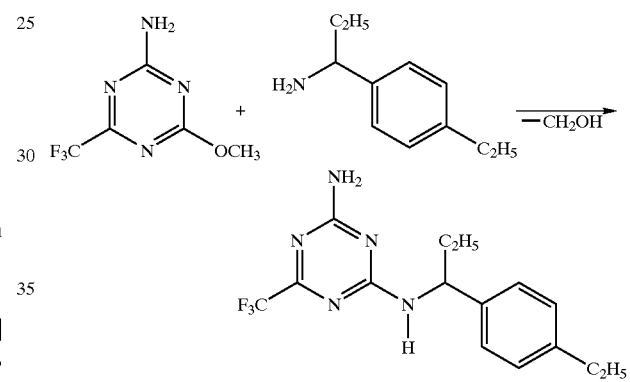

Using, for example, 2-amino- 4-(1-fluoro-1-methyl-ethyl)-6-[1-(2-methyl-phenyl)-ethylamino]-1,3,5-triazine and acetyl chloride as starting materials, the course of the reaction in the process (d) according to the invention can be illustrated by the following equation:

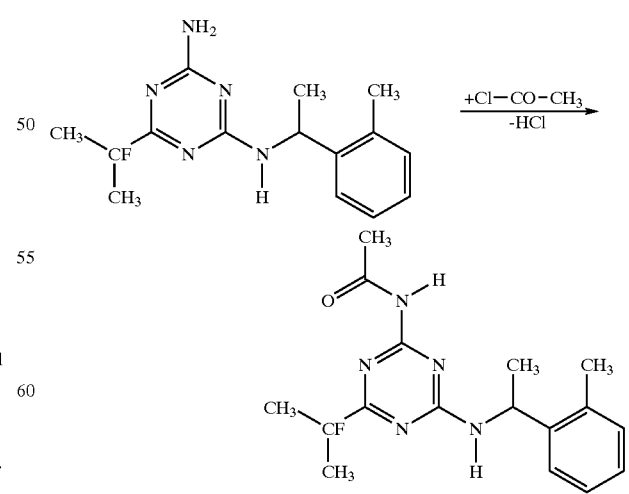

The formula (II) provides a general definition of the substituted biguanides to be used as starting materials in the process (a) according to the invention for preparing compounds of the formula (I. In the formula (II), $R^1$, $R^2$, $R^3$ and X each preferably or in particular have those meanings which have already been mentioned above, in connection with the description of the compounds of the formula (I) according to the invention, as being preferred or as being particularly preferred for $R^1$, $R^2$, $R^3$ and X.

Examples of the substituted biguanides of the formula (II)—where preference is in each case given to the racemates, the R enantiomers and the S enantiomers—which may be mentioned are:

1-(1-(2-fluoro-phenyl)-ethyl)-, 1-(1-(3-fluoro-phenyl)-ethyl)-, 1-(1-(4-fluoro-phenyl)-ethyl)-, 1-(1-(2-chloro-phenyl)-ethyl)-, 1-(1-(3-chloro-phenyl)-ethyl)-, 1-(1-(4-chloro-phenyl)-ethyl)-, 1-(1-(2-bromo-phenyl)-ethyl)-, 1-(1-(3-bromo-phenyl)-ethyl)-, 1-(1-(4-bromo-phenyl)-ethyl)-, 1-(1-(2-nitro-phenyl)-ethyl)-, 1-(1-(3-nitro-phenyl)-ethyl)-, 1-(1-(4-nitro-phenyl)-ethyl)-, 1-(1-(2-methyl-phenyl)-ethyl)-, 1-(1-(3-methyl-phenyl)-ethyl)-, 1-(1-(4-methyl-phenyl)-ethyl)-, 1-(1-(2-trifluoromethyl-phenyl)-ethyl)-, 1-(1-(3-trifluoromethyl-phenyl)-ethyl)-, 1-(1-(4-trifluoromethyl-phenyl)-ethyl)-, 1-(1-(2-methoxy-phenyl)-ethyl)-, 1-(1-(3-methoxy-phenyl)-ethyl)-, 1-(1-(4-methoxy-phenyl)-ethyl)-, 1-(1-(2-difluoromethoxy-phenyl)-ethyl)-, 1-(1-(2-difluoromethoxy-phenyl)-ethyl)-, 1-(1-(2-difluoromethoxy-phenyl)-ethyl)-, 1-(1-(2-trifluoromethoxy-phenyl)-ethyl)-, 1-(1-(3-trifluoromethoxy-phenyl)-ethyl)-, 1-(1-(4-trifluoromethoxy-phenyl)-ethyl)-, 1-(1-(2-methoxycarbonyl-phenyl)-ethyl)-, 1-(1-(2-ethoxycarbonyl-phenyl)-ethyl)-, 1-(1-(4-methoxycarbonyl-phenyl)-ethyl)-, 1-(1-(4-ethoxycarbonyl-phenyl)-ethyl)-, 1-(1-(2-methylthio-phenyl)-ethyl)-, 1-(1-(4-methylthio-phenyl)-ethyl)-, 1-(1-(2-methylsulphinyl-phenyl)-ethyl)-, 1-(1-(4-methylsulphinyl-phenyl)-ethyl)-, 1-(1-(2-methylsulphonyl-phenyl)-ethyl)- and 1-(1-(4-methylsulphonyl-phenyl)-ethyl)-biguanide.

Suitable acid adducts of compounds of the formula (II) are their addition products with protic acids, such as, for example with hydrogen chloride, hydrogen bromide, sulphuric acid, methanesulphonic acid, benzenesulphonic acid and p-toluenesulphonic acid.

The starting materials of the general formula (II), with the exception of 1-[1-(4-trifluoromethyl-phenyl)-ethyl]-biguanide (cf. U.S. Pat. No. 3,860,648), have hitherto not been disclosed in the literature; with the exception of 1-[1-(4-trifluoromethyl-phenyl)-ethyl]-biguanide, they also form, as novel substances, part of the subject-matter of the present application.

The substituted biguanides of the general formula (II) are obtained when substituted phenylalkylamines of the general formula (VII),

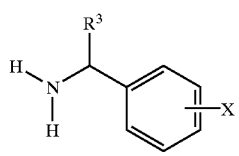

(VII)

in which
 $R^3$ and X are each as defined above
and/or acid adducts of compounds of the general formula (VII), such as, for example, the hydrochlorides are reacted with cyanoguanidines of the general formula (IX)

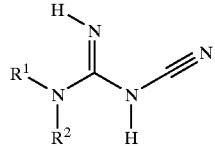

(IX)

in which
 $R^1$ and $R^2$ are each as defined above,
if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf. U.S. Pat. No. 3,860,648, Preparation Examples).

The substituted phenylalkylamines of the formula (VII) required as precursors for this purpose are known and/or can be prepared by processes known per se (cf. DE 2442845; DE 4038356; EP 490175, U.S. Pat. No. 5,300,437; J. Am. Chem. Soc. 105 (1983), 1578–1584; Tetrahedron: Asymmetry 4 (1993), 2093–2100; Biotechnol. Tech. 10 (1996), 335–338 —cited in Chem. Abstracts 125: 58008).

The cyanoguanidines of the formula (IX) are known chemicals for synthesis.

The formula (III) provides a general definition of the alkoxycarbonyl compounds further to be used as starting materials in the process (a) according to the invention for preparing compounds of the formula (I). In the formula (III), Z preferably or in particular has that meaning which has already been mentioned above,. in connection with the description of the compounds of the formula (I) according to the invention, as being preferred or as being particularly preferred for Z; R' preferably represents alkyl having 1 to 4 carbon atoms, and in particular represents methyl or ethyl.

The starting materials of the formula (III) are known chemicals for synthesis.

The formula (IV) provides a general definition of the substituted aminotriazines to be used as starting materials in the process (b) according to the invention for preparing compounds of the formula (I). In the formula (IV), $R^3$, X and Z each preferably or in particular have those meanings which have already been mentioned above, in connection with the description of the compounds of the formula (I according to the invention, as being preferred or as being particularly preferred for $R^3$, X and Z; $X^1$ preferably represents fluorine, chlorine, bromine or $C_1$–$C_4$-alkoxy, and in particular represents fluorine, chlorine, methoxy or ethoxy.

The starting materials of the general formula (IV) are known and/or can be prepared by processes known per se (cf. EP 300313).

The formula (V) provides a general definition of the nitrogen compounds further to be used as starting materials in the process (b) according to the invention for preparing compounds of the formula (I). In the formula (V), $R^1$ and $R^2$ each preferably or in particular have those meanings which have already been mentioned above, in connection with the description of the compounds of the formula (I) according to the invention, as being preferred or as being particularly preferred for $R^1$ and $R^2$.

The starting materials of the general formula (V) are known chemicals for synthesis.

The formula (VI) provides a general definition of the substituted aminotriazines to be used as starting materials in the process (c) according to the invention for preparing compounds of the formula (I). In the formula (VI), $R^1$, $R^2$ and Z preferably or in particular have those meanings which have already been mentioned above, in connection with the description of the compounds of the formula (I) according to the invention, as being preferred or as being particularly preferred for $R^1$, $R^2$ and Z; $X^2$ preferably represents fluorine, chlorine, bromine or $C_1$–$C_4$-alkoxy, and in particular represents fluorine, chlorine, methoxy or ethoxy.

The starting materials of the general formula (VI) are known and/or can be prepared by processes known per se (cf. WO 95/11237).

The formula (VII) provides a general definition of the amino compounds further to be used as starting materials in the process (c) according to the invention. In the formula (VII), $R^3$ and X each preferably or in particular have those meanings which have already been mentioned above, in connection with the description of the compounds of the formula (IV) according to the invention, as being preferred or as being particularly preferred for $R^3$ and X.

The starting materials of the general formula (VII) are known and/or can be prepared by processes known per se (cf. DE 2442845; DE 4038356; EP 490175; U.S. Pat. No. 5,300,437; J. Am. Chem. Soc. 105 (1983), 1578–1584; Tetrahedron: Asymmetry 4 (1993), 2095–2100; Biotechnol. Tech. 10 (1996), 335–338 —cited in Chem. Abstracts 125: 58008).

The formula (Ia) provides a general definition of the 2,4-diamino-1,3,5-triazines to be used as starting materials in the process (d) according to the invention for preparing compounds of the formula (I. In the formula (Ia), $R^1$, $R^3$, X and Z each preferably or in particular have those meanings which have already been mentioned above, in connection with the description of the compounds of the formula (I) according to the invention, as being preferred or as being particularly preferred for $R^1$, $R^3$, X and Z.

As novel compounds, the starting materials of the general formula (Ia) also form part of the subject-matter of the present application; they can be prepared by the processes (a), (b) or (c) according to the invention.

The formula (VIII) provides a general definition of the alkylating, acylating or sulphonylating agents further to be used as starting materials in the process (d) according to the invention for preparing compounds of the formula (I). In the formula (VIII), $R^2$ preferably or in particular has that meaning which has already been mentioned above, in connection with the description of the compounds of the formula (I) according to the invention, as being preferred or as being particularly preferred for $R^2$; Y preferably represents fluorine, chlorine, bromine, iodine, methoxy, ethoxy, methoxysulphonyloxy, ethoxysulphonyloxy, acetyloxy or propionyloxy.

The starting materials of the general formula (VIII) are known chemicals for synthesis.

If appropriate, the processes according to the invention for preparing the compounds of the formula (I) are carried out using a reaction auxiliary. Suitable reaction auxiliaries for the processes (a), (b), (c) and (d) are the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; firthermore also basic organic nitrogen compounds, such as, for example, trimethylamine, triethylamine, tripropylamine, tributylamine, ethyl-diisopropylmine, N,N-dimethyl-cyclohexylamine, dicyclohexylamine, ethyl-dicyclohexylamine, N,N-dimethylaniline, N,N-dimethyl-benzylamine, pyridine, 2-methyl-, 3-methyl-, 4-ethyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-di-azabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a), (b), (c) and (d) according to the invention are, if appropriate, inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-form-anilide, N-methyl-pyrrolidone or hexamethylphosphoric triamide; esters, such as methyl acetate, ethyl acetate, n- or -i- propyl acetate, n-, i- or s-butyl acetate; sulphoxides, such as dimethyl sulphoxide; alcohols, such as methanol, ethanol, n- or i-propanol, n- i-, s- or t-butanol, ethylene glycol monomethyl ether, ethylene glycol monoethyl ether, diethylene glycol monomethyl ether, diethylene glycol monoethyl ether, mixtures thereof with water or pure water.

In the practice of the processes (a), (b), (c) and (d) according to the invention, the reaction temperatures can be varied over a relatively wide range. Generally, the reaction is carried out at temperatures between 0° C. and 300° C., preferably between 10° C. and 250° C.

The processes (a), (b), (c) and (d) according to the invention are generally carried out at atmospheric pressure. However, it is also possible to carry out the processes according to the invention under elevated or reduced pressure—generally between 0.1 bar and 10 bar.

In the practice of the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred for several hours at the temperature required. Work-up is carried out by conventional methods (cf. the Preparation Examples).

The active compounds according to the invention can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera and Phalaris.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective control of weeds in annual cultures.

The compounds of the formula (I) according to the invention are suitable in particular for selectively controlling monocotyledonous and dicotyledonous weeds in monocotyledonous and dikotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfiron(-methyl), ethofumesate, ethoxyfen, etobenzanid, fenoxaprop-ethyl, flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulftiron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium) quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the Examples below.

PREPARATION EXAMPLES

Example 1

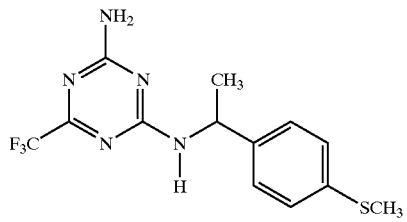

(Process (a))

At 20° C. to 35° C., a solution of 4.6 g (85 mmol) of sodium methoxide in 15 ml of methanol is added dropwise with stirring to a mixture of 20.4 g (80 mmol) of 1-[1-(4-methylthio-phenyl)-ethyl]-biguanide (racemic), 13 g (80 mmol) of ethyl trifluoroacetate and 100 ml of methanol, and the reaction mixture is then stirred at room temperature (approximately 20° C.) for another 15 hours. The mixture is then shaken with methylene chloride and water and the organic phase is separated off, washed with 1% strength aqueous sodium hydroxide solution, dried with sodium sulphate and filtered. The filtrate is carefully concentrated under water pump vacuum, the residue is crystallized by digestion with ligroin and the product is isolated by filtration with suction.

This gives 12.4 g (47% of theory) of 2-amino4-trifluoromethyl-6-[1-(4-methylthio-phenyl)-ethylamino]-1,3,5-triazine (racemate) of melting point 111° C.

Example 2

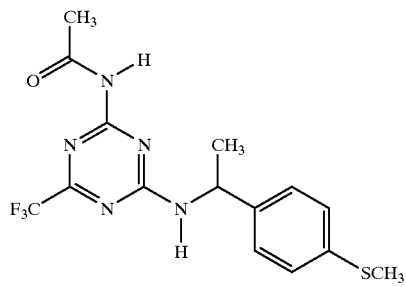

(Process (d))

A mixture of 16.5 g (50 mmol) of 2-amino4-trifluoromethyl-6-[1-(4-methylthio-phenyl)-ethylamino]-1,3,5-triazine (racemic) and 60 ml of acetic anhydride is stirred at 130° C. for 3 hours, cooled to room temperature (approximately 20° C.) and then admixed with 200 ml of water and stirred at room temperature for a further hour. The resulting crystalline product is then isolated by filtration with suction.

This gives 13.3 g (72% of theory) of 2-acetylamino-4-trifluoromethyl-6-[1-(4-methylthio-phenyl)-ethylamino]-1,3,5-triazine (racemate) of melting point 132° C.

Example 3

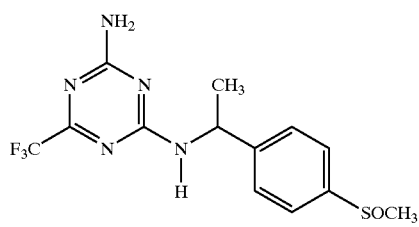

(Subsequent Reaction)

Over a period of 30 minutes, 5 g of 3-chloro-perbenzoic acid (about 60% stength) are added with stirring to a mixture of 6.6 g (20 mmol) of 2-amino-4-trifluoromethyl- 6-[1-(4-methylthio-phenyl)-ethylamino]-1,3,5-triazine (racemic) and 80 ml of dichloromethane and the reaction mixture is then stirred at room temperature (approximately 20° C.) for another hour. The mixture is subsequently washed with water and then with 5% strength aqueous ammonia solution, dried with sodium sulphate and filtered. The solvent is carefully distilled off from the filtrate under water pump vacuum.

This gives 4.4 g (64% of theory) of 2-amino-4-trifluoromethyl-6-[1-(4-methylsulphinyl-phenyl)-ethylamino]-1,3,5-triazine (racemate) as a solid product of melting point 220° C. (decomposition).

By the methods of Preparation Examples 1 to 3, and in accordance with the general description of the preparation processes according to the invention, it is also possible to prepare, for example, the compounds of the formula (I) listed in Table 1 below.

TABLE 1

Examples of compounds of the formula (I)

(I) [structure: triazine with $R^1R^2N$- and -NH-CH($R^3$)-phenyl-X substituents, and Z substituent]

| Ex. No. | $R^1$ | $R^2$ | $R^3$ | (Position-) X | Z | Physical data and stereochemical specifications |
|---|---|---|---|---|---|---|
| 4 | H | H | $CH_3$ | (4-) Cl | Cl | m.p.: 133° C. (R enantiomer) |
| 5 | H | H | $CH_3$ | (4-) Cl | Cl | m.p.: 133° C. (S enantiomer) |
| 6 | H | $SO_2CH_3$ | $CH_3$ | (4-) Cl | Cl | (amorphous) (R enantiomer) |
| 7 | H | $SO_2CH_3$ | $CH_3$ | (4-) Cl | Cl | (amorphous) (S enantiomer) |
| 8 | H | H | $CH_3$ | (4-) Cl | Cl | m.p.: 193° C. (racemate) |
| 9 | H | $SO_2CH_3$ | $CH_3$ | (4-) Cl | Cl | (amorphous) (racemate) |
| 10 | H | H | $CH_3$ | (4-) Cl | $SCH_3$ | (amorphous) (R enantiomer) |
| 11 | H | H | $CH_3$ | (4-) Cl | $SCH_3$ | (amorphous) (S enantiomer) |
| 12 | H | H | $CH_3$ | (4-) Cl | $SCH_3$ | (amorphous) (racemate) |
| 13 | H | H | $CH_3$ | (4-) Cl | $CHFCH_3$ | (amorphous) (S enantiomer) $[\alpha]_D^{20} = -133.54$ |
| 14 | H | H | $CH_3$ | (4-) Cl | $CHFCH_3$ | (amorphous) (R enantiomer) $[\alpha]_D^{20} = +129.84$ |
| 15 | H | H | $CH_3$ | (4-) Cl | $CF_3$ | m.p.: 119° C. (S enantiomer) $[\alpha]_D^{20} = -175.39$ |
| 16 | H | H | $CH_3$ | (4-) Cl | $CF(CH_3)_2$ | (amorphous) (S enantiomer) $[\alpha]_D^{20} = -100.61$ |
| 17 | H | H | $CH_3$ | (4-) Cl | $CF_2CF_3$ | (amorphous) (S enantiomer) $[\alpha]_D^{20} = -121.76$ |
| 18 | H | H | $CH_3$ | (4-) $CH_3$ | $CHFCH_3$ | m.p.: 116° C. (S enantiomer) $[\alpha]_D^{20} = -156.85$ |
| 19 | H | H | $CH_3$ | (4-) $CH_3$ | $CF(CH_3)_2$ | (amorphous) (S enantiomer) $[\alpha]_D^{20} = -117.31$ |
| 20 | H | H | $CH_3$ | (4-) $CH_3$ | $CF_3$ | m.p.: 140° C. (S enantiomer) $[\alpha]_D^{20} = -193.46$ |
| 21 | H | H | $CH_3$ | (4-) Cl | $CF_3$ | m.p.: 119° C. (R enantiomer) $[\alpha]_D^{20} = +169.03$ |
| 22 | H | H | $CH_3$ | (4-) Cl | $CF(CH_3)_2$ | (amorphous) (R enantiomer) $[\alpha]_D^{20} = +107.30$ |
| 23 | H | H | $CH_3$ | (4-) Cl | $CF_2CF_3$ | (amorphous) (R enantiomer) $[\alpha]_D^{20} = +18.77$ |
| 24 | H | H | $CH_3$ | (4-) $SO_2CH_3$ | $CF_3$ | m.p.: 230° C. (racemate) |
| 25 | H | $COCH_3$ | $CH_3$ | (4-) $SOCH_3$ | $CF_3$ | m.p.: 162° C. (racemate) |
| 26 | H | $COCH_3$ | $CH_3$ | (4-) $SO_2CH_3$ | $CF_3$ | m.p.: 235° C. (racemate) |
| 27 | H | H | $CH_3$ | (4-) $SCH_3$ | $CH_3$ | (amorphous) (racemate) |

TABLE 1-continued

Examples of compounds of the formula (I)

(I)

| Ex. No. | R¹ | R² | R³ | (Position-) X | Z | Physical data and stereochemical specifications |
|---|---|---|---|---|---|---|
| 28 | H | H | CH$_3$ | (4-) SOCH$_3$ | CH$_3$ | (amorphous) (racemate) |
| 29 | H | H | CH$_3$ | (4-) SO$_2$CH$_3$ | CH$_3$ | (amorphous) (racemate) |
| 30 | H | COCH$_3$ | CH$_3$ | (4-) SCH$_3$ | CH$_3$ | m.p.: 170° C. (racemate) |
| 31 | H | COCH$_3$ | CH$_3$ | (4-) SOCH$_3$ | CH$_3$ | m.p.: 193° C. (racemate) |
| 32 | H | COCH$_3$ | CH$_3$ | (4-) SO$_2$CH$_3$ | CH$_3$ | m.p.: 205° C. (racemate) |
| 33 | H | H | CH$_3$ | (4-) SCH$_3$ | CHFCH$_3$ | (amorphous) (racemate) |
| 34 | H | H | CH$_3$ | (4-) SOCH$_3$ | CHFCH$_3$ | (amorphous) (racemate) |
| 35 | H | H | CH$_3$ | (4-) SO$_2$CH$_3$ | CHFCH$_3$ | (amorphous) (racemate) |
| 36 | H | COCH$_3$ | CH$_3$ | (4-) SCH$_3$ | CHFCH$_3$ | m.p.: 121° C. (racemate) |
| 37 | H | COCH$_3$ | CH$_3$ | (4-) SOCH$_3$ | CHFCH$_3$ | m.p.: 193° C. (racemate) |
| 38 | H | COCH$_3$ | CH$_3$ | (4-) SO$_2$CH$_3$ | CHFCH$_3$ | m.p.: 212° C. (racemate) |
| 39 | H | H | CH$_3$ | (4-) SCH$_3$ | CF(CH$_3$)$_2$ | m.p.: 80° C. (racemate) |
| 40 | H | H | CH$_3$ | (4-) SOCH$_3$ | CF(CH$_3$)$_2$ | m.p.: 215° C. (racemate) |
| 41 | H | H | CH$_3$ | (4-) SO$_2$CH$_3$ | CF(CH$_3$)$_2$ | m.p.: 170° C. (racemate) |
| 42 | H | COCH$_3$ | CH$_3$ | (4-) SCH$_3$ | CF(CH$_3$)2 | m.p.: 102° C. (racemate) |
| 43 | H | COCH$_3$ | CH$_3$ | (4-) SOCH$_3$ | CF(CH$_3$)$_2$ | m.p.: 192° C. (racemate) |
| 44 | H | COCH$_3$ | CH$_3$ | (4-) SO$_2$CH$_3$ | CF(CH$_3$)$_2$ | m.p.: 195° C. (racemate) |
| 45 | H | H | CH$_3$ | (3-) Br | CF(CH$_3$)$_2$ | m.p.: 136° C. (racemate) |
| 46 | H | H | CH$_3$ | (3-) CF$_3$ | CF(CH$_3$)$_2$ | m.p.: 137° C. (racemate) |
| 47 | H | H | CH$_3$ | (4-) CH$_3$ | CF(CH$_3$)$_2$ | m.p.: 106° C. (racemate) |
| 48 | H | H | CH$_3$ | (3-) CH$_3$ | CF(CH$_3$)$_2$ | n$_D^{20}$ = 1.5440 (racemate) |
| 49 | H | H | CH$_3$ | (4-) C(CH$_3$)$_3$ | CF(CH$_3$)$_2$ | m.p.: 160° C. (racemate) |
| 50 | H | H | CH$_3$ | (2-) CH$_3$ | CF(CH$_3$)$_2$ | m.p.: 117° C. (racemate) |
| 51 | H | H | CH$_3$ | (4-) SCH$_3$ | OH | m.p.: >240° C. (racemate) |
| 52 | H | H | CH$_3$ | (4-) CH$_3$ | CF$_3$ | (R enantiomer) |
| 53 | H | COCH$_3$ | CH$_3$ | (4-) CH$_3$ | CF$_3$ | (R enantiomer) |
| 54 | H | COCH$_3$ | CH$_3$ | (4-) CH$_3$ | CF$_3$ | (S enantiomer) |
| 55 | H | H | CH$_3$ | (4-) CH$_3$ | CHFCH$_3$ | (R enantiomer) |
| 56 | H | COCH$_3$ | CH$_3$ | (4-) CH$_3$ | CHFCH$_3$ | (R enantiomer) |
| 57 | H | COCH$_3$ | CH$_3$ | (4-) CH$_3$ | CHFCH$_3$ | (S enantiomer) |
| 58 | H | H | CH$_3$ | (4-) CH$_3$ | CF(CH$_3$)$_2$ | (R enantiomer) |
| 59 | H | COCH$_3$ | CH$_3$ | (4-) CH$_3$ | CF(CH$_3$)$_2$ | (R enantiomer) |
| 60 | H | COCH$_3$ | CH$_3$ | (4-) CH$_3$ | CF(CH$_3$)$_2$ | (S enantiomer) |
| 61 | H | H | CH$_3$ | (4-) F | CF$_3$ | (racemate) |
| 62 | H | H | CH$_3$ | (4-) F | CF$_3$ | (R enantiomer) |
| 63 | H | H | CH$_3$ | (4-)F | CF$_3$ | (S enantiomer) |

TABLE 1-continued

Examples of compounds of the formula (I)

$$\text{(I)}$$

Structure: 1,3,5-triazine with substituents — NR¹R² at one position, Z at another, and NH-CH(R³)-C₆H₄-X at the third.

| Ex. No. | R¹ | R² | R³ | (Position-) X | Z | Physical data and stereochemical specifications |
|---|---|---|---|---|---|---|
| 64 | H | COCH₃ | CH₃ | (4-) F | CF₃ | (racemate) |
| 65 | H | COCH₃ | CH₃ | (4-) F | CF₃ | (R enantiomer) |
| 66 | H | COCH₃ | CH₃ | (4-) F | CF₃ | (S enantiomer) |
| 67 | H | H | CH₃ | (4-) F | CF(CH₃)₂ | (racemate) |
| 68 | H | H | CH₃ | (4-) F | CF(CH₃)₂ | (R enantiomer) |
| 69 | H | H | CH₃ | (4-) F | CF(CH₃)₂ | (S enantiomer) |
| 70 | H | COCH₃ | CH₃ | (4-) F | CF(CH₃)₂ | (racemate) |
| 71 | H | COCH₃ | CH₃ | (4-) F | CF(CH₃)₂ | (R enantiomer) |
| 72 | H | COCH₃ | CH₃ | (4-) F | CF(CH₃)₂ | (S enantiomer) |
| 73 | H | H | CH₃ | (4-) F | CHFCH₃ | (racemate) |
| 74 | H | H | CH₃ | (4-) F | CHFCH₃ | (R enantiomer) |
| 75 | H | H | CH₃ | (4-) F | CHFCH₃ | (S enantiomer) |
| 76 | H | COCH₃ | CH₃ | (4-) F | CHFCH₃ | (racemate) |
| 77 | H | COCH₃ | CH₃ | (4-) F | CHFCH₃ | (R enantiomer) |
| 78 | H | COCH₃ | CH₃ | (4-) F | CHFCH₃ | (S enantiomer) |
| 79 | H | H | CH₃ | (4-) OCH₃ | CF₃ | (amorphous) (racemate) |
| 80 | H | H | CH₃ | (4-) OCH₃ | CF₃ | (amorphous) (R enantiomer) |
| 81 | H | H | CH₃ | (4-)OCH₃ | CF₃ | m.p.: 111° C. (S enantiomer) |
| 82 | H | COCH₃ | CH₃ | (4-) OCH₃ | CF₃ | m.p.: 130° C. (racemate) |
| 83 | H | COCH₃ | CH₃ | (4-) OCH₃ | CF₃ | m.p.: 105° C. (R enantiomer) |
| 84 | H | COCH₃ | CH₃ | (4-) OCH₃ | CF₃ | m.p.: 108° C. (S enantiomer) |
| 85 | H | H | C₂H₅ | (4-) Cl | CF₃ | m.p.: 145° C. (racemate) |
| 86 | H | H | C₂H₅ | (4-) Cl | CF₃ | (amorphous) (R enantiomer) |
| 87 | H | H | C₂H₅ | (4-) Cl | CF₃ | (amorphous) (S enantiomer) |
| 88 | H | COCH₃ | C₂H₅ | (4-) Cl | CF₃ | m.p.: 128° C. (racemate) |
| 89 | H | COCH₃ | C₂H₅ | (4-) Cl | CF₃ | m.p.: 108° C. (R enantiomer) |
| 90 | H | COCH₃ | C₂H₅ | (4-) Cl | CF₃ | m.p.: 116° C. (S enantiomer) |
| 91 | H | H | CH₃ | (4-) Cl | C₂H₅ | (amorphous) (racemate) |
| 92 | H | H | CH₃ | (4-) Cl | C₃H₇-i | (amorphous) (racemate) |
| 93 | H | H | CH₃ | (4-) Cl | CHFCF₃ | (amorphous) (racemate) |
| 94 | H | H | CH₃ | (4-) Cl | CHCl₂ | (amorphous) (racemate) |
| 95 | H | H | CH₃ | (4-) Cl | CH₂Cl | m.p.: 149° C. (racemate) |
| 96 | H | H | CH₃ | (4-) Cl | CHClCH₃ | (amorphous) (racemate) |
| 97 | H | H | CH₃ | (4-) Cl | CCl₂CH₃ | (amorphous) (racemate) |
| 98 | H | H | CH₃ | (4-) Cl | CH₂OCH₃ | m.p.: 149° C. (racemate) |
| 99 | H | H | CH₃ | (4-) Cl | CF₃ | m.p.: 99° C. (racemate) |
| 100 | H | H | CH₃ | (4-) SCH₃ | CH₂OCH₃ | m.p.: 113° C. (racemate) |

TABLE 1-continued

Examples of compounds of the formula (I)

$$\text{(I)}$$

Structure: A 1,3,5-triazine with $R^1R^2N-$ and $-NH-CH(R^3)-C_6H_4-X$ substituents, and $Z$ substituent.

| Ex. No. | $R^1$ | $R^2$ | $R^3$ | (Position-) X | Z | Physical data and stereochemical specifications |
|---|---|---|---|---|---|---|
| 101 | H | H | $CH_3$ | (4-) $SOCH_3$ | $CH_2OCH_3$ | (amorphous) (racemate) |
| 102 | H | H | $CH_3$ | (4-) $SO_2CH_3$ | $CH_2OCH_3$ | m.p.: 177° C. (racemate) |
| 103 | H | $COCH_3$ | $CH_3$ | (4-) $SCH_3$ | $CH_2OCH_3$ | m.p.: 141° C. (racemate) |
| 104 | H | $COCH_3$ | $CH_3$ | (4-) $SOCH_3$ | $CH_2OCH_3$ | m.p.: 182° C. (racemate) |
| 105 | H | $COCH_3$ | $CH_3$ | (4-) $SO_2CH_3$ | $CH_2OCH_3$ | m.p.: 185° C. (racemate) |
| 106 | H | H | $CH_3$ | (4-) $SOCH_3$ | OH | m.p.: >250° C. (racemate) |
| 107 | H | H | $CH_3$ | (4-) $SO_2CH_3$ | OH | m.p.: >250° C. (racemate) |
| 108 | H | H | $CH_3$ | (4-) $SCH_3$ | $CHCl_2$ | m.p.: 125° C. (racemate) |
| 109 | H | H | $CH_3$ | (4-) $SOCH_3$ | $CHCl_2$ | m.p.: 161° C. (racemate) |
| 110 | H | H | $CH_3$ | (4-) $SO_2CH_3$ | $CHCl_2$ | (amorphous) (racemate) |
| 111 | H | $COCH_3$ | $CH_3$ | (4-) $SCH_3$ | $CHCl_2$ | m.p.: 134° C. (racemate) |
| 112 | H | $COCH_3$ | $CH_3$ | (4-) $SOCH_3$ | $CHCl_2$ | m.p.: 187° C. (racemate) |
| 113 | H | $COCH_3$ | $CH_3$ | (4-) $SO_2CH_3$ | $CHCl_2$ | m.p.: 221° C. (racemate) |
| 114 | H | H | $CH_3$ | (4-) $SCH_3$ | $CH_2Cl$ | m.p.: 109° C. (racemate) |
| 115 | H | H | $CH_3$ | (4-) $SOCH_3$ | $CH_2Cl$ | (amorphous) (racemate) |
| 116 | H | H | $CH_3$ | (4-) $SO_2CH_3$ | $CH_2Cl$ | (amorphous) (racemate) |
| 117 | H | $COCH_3$ | $CH_3$ | (4-) $SCH_3$ | $CH_2Cl$ | m.p.: 139° C. (racemate) |
| 118 | H | $COCH_3$ | $CH_3$ | (4-) $SOCH_3$ | $CH_2Cl$ | m.p.: 151° C. (racemate) |
| 119 | H | $COCH_3$ | $CH_3$ | (4-) $SO_2CH_3$ | $CH_2Cl$ | m.p.: 172° C. (racemate) |
| 120 | H | H | $CH_3$ | (4-) $SCH_3$ | $CHClCH_3$ | m.p.: 103° C. (racemate) |
| 121 | H | H | $CH_3$ | (4-) $SOCH_3$ | $CHClCH_3$ | m.p.: 214° C. (racemate) |
| 122 | H | H | $CH_3$ | (4-) $SO_2CH_3$ | $CHClCH_3$ | m.p.: 145° C. (racemate) |
| 123 | H | $COCH_3$ | $CH_3$ | (4-) $SCH_3$ | $CHClCH_3$ | m.p.: 111° C. (racemate) |
| 124 | H | $COCH_3$ | $CH_3$ | (4-) $SOCH_3$ | $CHClCH_3$ | m.p.: 155° C. (racemate) |
| 125 | H | $COCH_3$ | $CH_3$ | (4-) $SO_2CH_3$ | $CHClCH_3$ | m.p.: 179° C. (racemate) |
| 126 | H | H | $CH_3$ | (4-) $SCH_3$ | $CCl_2CH_3$ | m.p.: 133° C. (racemate) |
| 127 | H | H | $CH_3$ | (4-) $SOCH_3$ | $CCl_2CH_3$ | (amorphous) (racemate) |
| 128 | H | H | $CH_3$ | (4-) $SOCH_3$ | $CCl_2CH_3$ | (amorphous) (racemate) |
| 129 | H | $COCH_3$ | $CH_3$ | (4-) $SCH_3$ | $CCl_2CH_3$ | m.p.: 114° C. (racemate) |
| 130 | H | $COCH_3$ | $CH_3$ | (4-) $SOCH_3$ | $CCl_2CH_3$ | m.p.: 255° C. (racemate) |

TABLE 1-continued

Examples of compounds of the formula (I)

(I)

| Ex. No. | R¹ | R² | R³ | (Position-) X | Z | Physical data and stereochemical specifications |
|---|---|---|---|---|---|---|
| 131 | H | COCH₃ | CH₃ | (4-) SOCH₃ | CCl₂CH₃ | m.p.: 185° C. (racemate) |
| 132 | H | H | CH₃ | (4-) SCH₃ | C₃F₇-n | (amorphous) (racemate) |
| 133 | H | H | CH₃ | (4-) SOCH₃ | C₃F₇-n | m.p.: 153° C. (racemate) |
| 134 | H | H | CH₃ | (4-) SOCH₃ | C₃F₇-n | (amorphous) (racemate) |
| 135 | H | COCH₃ | CH₃ | (4-) SCH₃ | C₃F₇-n | m.p.: 124° C. (racemate) |
| 136 | H | COCH₃ | CH₃ | (4-) SOCH₃ | C₃F₇-n | m.p.: 185° C. (racemate) |
| 137 | H | COCH₃ | CH₃ | (4-) SOCH₃ | C₃F₇-n | m.p.: 210° C. (racemate) |
| 138 | H | H | CH₃ | (4-) Cl | C₂F₅ | m.p.: 130° C. (racemate) |
| 139 | H | H | CH₃ | (4-) Cl | OH | m.p. >260° C. (racemate) |
| 140 | H | COCH₃ | CH₃ | (4-) Cl | C₂F₅ | m.p.: 163° C. (racemate) |
| 141 | H | COCH₃ | CH₃ | (4-) Cl | C₂H₅ | m.p.: 185° C. (racemate) |
| 142 | H | COCH₃ | CH₃ | (4-) Ci | CHFCF₃ | m.p.: 165° C. (racemate) |
| 143 | H | COCH₃ | CH₃ | (4-) Cl | CH₂OCH₃ | m.p.: 187° C. (racemate) |
| 144 | H | COCH₃ | CH₃ | (4-) Cl | CH₂Cl | m.p.: 153° C. (reacemate) |
| 145 | H | COCH₃ | CH₃ | (4-) Cl | CHCl₂ | m.p.: 132° C. (racemate) |
| 146 | H | COCH₃ | CH₃ | (4-) Cl | CHClCH₃ | m.p.: 126° C. (racemate) |
| 147 | H | COCH₃ | CH₃ | (4-) Cl | CCl₂CH₃ | m.p.: 159° C. (racemate) |
| 148 | H | COCH₃ | CH₃ | (4-) Cl | OH | m.p. >240° C. (racemate) |
| 149 | H | H | CH₃ | (4-) Cl | CHCl₂ | m.p.: 152° C. (R enantiomer) |
| 150 | H | COCH₃ | CH₃ | (4-) Cl | CHCl₂ | m.p.: 126° C. (R enantiomer) |
| 151 | H | H | CH₃ | (4-) Cl | CH₂Cl | (amorphous) (R enantiomer) |
| 152 | H | COCH₃ | CH₃ | (4-) Cl | CH₂Cl | m.p.: 153° C. (R enantiomer) |
| 153 | H | H | CH₃ | (4-) Cl | C₂H₅ | (amorphous) (R enantiomer) |
| 154 | H | COCH₃ | CH₃ | (4-) Cl | C₂H₅ | m.p.: 155° C. (R enantiomer) |
| 155 | H | H | CH₃ | (4-) Cl | CHFCF₃ | (amorphous) (R enantiomer) |
| 156 | H | COCH₃ | CH₃ | (4-) Cl | CHFCF₃ | m.p.: 154° C. (R enantiomer) |
| 157 | H | H | CH₃ | (4-) Cl | CHClCH₃ | (amorphous) (R enantiomer) |
| 158 | H | COCH₃ | CH₃ | (4-) Cl | CHClCH₃ | m.p.: 119° C. (R enantiomer) |
| 159 | H | H | CH₃ | (4-) Cl | CCl₂CH₃ | (amorphous) (R enantiomer) |
| 160 | H | COCH₃ | CH₃ | (4-) Cl | CCl₂CH₃ | m.p.: 118° C. (R enantiomer) |

TABLE 1-continued

Examples of compounds of the formula (I)

(I)

$$\text{Structure: } R^1R^2N\text{-triazine with } Z, \text{ and } NH\text{-CH}(R^3)\text{-phenyl-}X$$

| Ex. No. | R¹ | R² | R³ | (Position-) X | Z | Physical data and stereochemical specifications |
|---|---|---|---|---|---|---|
| 161 | H | H | CH₃ | (4-) Cl | CH₂OCH₃ | (amorphous) (R enantiomer) |
| 162 | H | COCH₃ | CH₃ | (4-) Cl | CH₂OCH₃ | m.p.: 132° C. (R enantiomer) |
| 163 | H | COCH₃ | CH₃ | (4-) Cl | C₂F₅ | m.p.: 110° C. (R enantiomer) |
| 164 | H | H | CH₃ | (4-) Cl | OH | m.p. >240° C. (R enantiomer) |
| 165 | H | COCH₃ | CH₃ | (4-) Cl | OH | m.p. >240° C. (R enantiomer) |
| 166 | H | H | CH₃ | (4-) Cl | C₂H₅ | (amorphous) (S enantiomer) |
| 167 | H | H | CH₃ | (4-) Cl | CHFCF₃ | (amorphous) (S enantiomer) |
| 168 | H | H | CH₃ | (4-) Cl | CHCl₂ | m.p.: 133° C. (S enantiomer) |
| 169 | H | H | CH₃ | (4-) Cl | CH₂Cl | m.p.: 138° C. (S enantiomer) |
| 170 | H | H | CH₃ | (4-) Cl | CH₂OCH₃ | (amorphous) (S enantiomer) |
| 171 | H | H | CH₃ | (4-) Cl | CHClCH₃ | (amorphous) (S enantiomer) |
| 172 | H | H | CH₃ | (4-) Cl | OH | mp. >240° C. (S enantiomer) |
| 173 | H | COCH₃ | CH₃ | (4-) Cl | C₂H₅ | m.p.: 182° C. (S enantiomer) |
| 174 | H | COCH₃ | CH₃ | (4-) Ci | CHFCF₃ | m.p.: 175° C. (S enantiomer) |
| 175 | H | COCH₃ | CH₃ | (4-) Cl | CHCl₂ | m.p.: 131° C. (S enantiomer) |
| 176 | H | COCH₃ | CH₃ | (4-) Cl | CH₂Cl | m.p.: 126° C. (S enantiomer) |
| 177 | H | COCH₃ | CH₃ | (4-) Cl | CHClCH₃ | m.p.: 110° C. (S enantiomer) |
| 178 | H | COCH₃ | CH₃ | (4-) Cl | CH₂OCH₃ | m.p.: 155° C. (S enantiomer) |
| 179 | H | H | CH₃ | (4-) Cl | H | m.p.: 178° C. (racemate) |
| 180 | H | H | CH₃ | (4-) Cl | CH₃ | (amorphous) (racemate) |
| 181 | H | H | CH₃ | (4-) Cl | CH=CH₂ | (amorphous) (racemate) |
| 182 | H | H | CH₃ | (4-) Cl | C₃H₇-n | (amorphous) (racemate) |
| 183 | H | COCH₃ | CH₃ | (4-) Cl | H | m.p.: 198° C. (racemate) |
| 184 | H | COCH₃ | CH₃ | (4-) Cl | CH₃ | m.p.: 155° C. (racemate) |
| 185 | H | COCH₃ | CH₃ | (4-) Cl | CH=CH₂ | m.p.: 142° C. (racemate) |
| 186 | H | COCH₃ | CH₃ | (4-) Cl | C₃H₇-n | m.p.: 153° C. (racemate) |
| 187 | H | COCH₃ | CH₃ | (4-) Cl | C₃H₇-i | m.p.: 136° C. (racemate) |
| 188 | H | H | CH₃ | (4-) Cl | C₅H₁₁-n | (amorphous) (racemate) |
| 189 | H | COCH₃ | CH₃ | (4-) Cl | C₅H₁₁-n | m.p.: 122° C. (racemate) |
| 190 | H | H | CH₃ | (4-) OCH₃ | CHFCH₃ | (amorphous) (racemate) |

TABLE 1-continued

Examples of compounds of the formula (I)

(I)

| Ex. No. | $R^1$ | $R^2$ | $R^3$ | (Position-) X | Z | Physical data and stereochemical specifications |
|---|---|---|---|---|---|---|
| 191 | H | COCH$_3$ | CH$_3$ | (4-) Cl | CF$_3$ | m.p.: 139° C. (racemate) |
| 192 | H | COCH$_3$ | CH$_3$ | (4-) Cl | CH$_3$ | m.p.: 144° C. (R enantiomer) |
| 193 | H | H | CH$_3$ | (4-) Cl | CHBrCH$_3$ | (amorphous) (R enantiomer) |
| 194 | H | H | CH$_3$ | (4-) Cl | CH(CH$_3$)$_2$ | (amorphous) (R enantiomer) |
| 195 | H | H | CH$_3$ | (4-) Cl | CH$_3$ | (amorphous) (R enantiomer) |
| 196 | H | H | CH$_3$ | (4-) Cl | H | (amorphous) (R enantiomer) |
| 197 | H | COCH$_3$ | CH$_3$ | (4-) Cl | CH(CH$_3$)$_2$ | (amorphous) (R enantiomer) |
| 198 | H | COCH$_3$ | CH$_3$ | (4-) Cl | CHBrCH$_3$ | (amorphous) (R enantiomer) |
| 199 | H | H | CH$_3$ | (4-) C$_6$H$_5$ | CF$_3$ | m.p.: 156° C. (racemate) |
| 200 | H | H | CH$_3$ | (4-) OC$_6$H$_5$ | CF$_3$ | m.p.: 62° C. (racemate) |
| 201 | H | H | C$_2$H$_5$ | (4-) Cl | CHFCH$_3$ | (amorphous) (racemate) |
| 202 | H | H | C$_2$H$_5$ | (4-) Cl | CF(CH$_3$)$_2$ | (amorphous) (racemate) |
| 203 | H | H | C$_2$H$_5$ | (4-) Cl | H | m.p.: 100° C. (D.) (racemate) |
| 204 | H | H | C$_2$H$_5$ | (4-) Cl | C$_2$H$_5$ | (amorphous) (racemate) |
| 205 | H | H | C$_2$H$_5$ | (4-) Cl | CHClCH$_3$ | (amorphous) (racemate) |
| 206 | H | COCH$_3$ | C$_2$H$_5$ | (4-) Cl | CHFCH$_3$ | (amorphous) (racemate) |
| 207 | H | COCH$_3$ | C$_2$H$_5$ | (4-) Cl | CF(CH$_3$)$_2$ | (amorphous) (racemate) |
| 208 | H | COCH$_3$ | C$_2$H$_5$ | (4-) Cl | H | m.p.: 179° C. (racemate) |
| 209 | H | H | CH$_3$ | (4-) Cl | CH$_2$CH$_2$OCH(CH$_3$)$_2$ | (amorphous) (racemate) |
| 210 | H | H | CH$_3$ | (4-) Cl | CH$_2$CH(OCH$_3$)$_2$ | (amorphous) (racemate) |
| 211 | H | H | CH$_3$ | (4-) Cl | cyclopropyl | (amorphous) (racemate) |
| 212 | H | H | CH$_3$ | (4-) Cl | C$_9$H$_{19}$ | (amorphous) (racemate) |
| 213 | H | H | CH$_3$ | (4-) Cl | CHBrCH$_3$ | (amorphous) (racemate) |
| 214 | H | H | CH$_3$ | (4-) Cl | CH$_2$SCH$_3$ | (amorphous) (racemate) |
| 215 | H | H | CH$_3$ | (4-) Cl | CH$_2$S(O)CH$_3$ | m.p.: 182° C. (racemate) |
| 216 | H | H | CH$_3$ | (4-) Cl | CH$_2$SO$_2$CH$_3$ | m.p.: 137° C. (racemate) |

TABLE 1-continued

Examples of compounds of the formula (I)

(I)

[Structure of formula (I)]

| Ex. No. | R¹ | R² | R³ | (Position-) X | Z | Physical data and stereochemical specifications |
|---|---|---|---|---|---|---|
| 217 | H | H | $CH_3$ | (4-) Cl | CHCH₃ \| OH | (amorphous) (racemate) |
| 218 | H | H | $CH_3$ | (4-) Cl | CHCH₃ \| OH | (amorphous) (S enantiomer) |
| 219 | H | $COCH_3$ | $CH_3$ | (4-) Cl | —⟨cyclopropyl⟩ | m.p.: 186° C. (racemate) |
| 220 | H | $COCH_3$ | $CH_3$ | (4-) Cl | $CH_2SCH_3$ | m.p.: 148° C. (racemate) |
| 221 | H | $COCH_3$ | $CH_3$ | (4-) Cl | $C_9H_{19}$ | m.p.: 103° C. (racemate) |
| 222 | H | $COCH_3$ | $CH_3$ | (4-) Cl | $CHBrCH_3$ | m.p.: 118° C. (racemate) |

"D." = Decomposition

It is also possible to prepare the compound listed in Table 1 as Example 99 for example in the following manner:

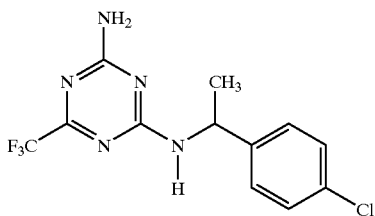

(Process (c))

A mixture of 2.0 g (12 mmol) of 1-(4-chloro-phenyl)-ethylamine (racemic) and 1.0 g (5.2 mmol) of 2-amino-4-methoxy-6-trifluoromethyl-1,3,5-triazine is heated under argon at 170° C. for 3 hours. After cooling, the mixture is taken up in methylene chloride and acidified with 1N hydrochloric acid. The organic phase is separated off, washed with water, dried with sodium sulphate and filtered. The filtrate is concentrated under water pump vacuum and the residue is purified by column chromatography (silica gel, ethyl acetate).

This gives 1.29 g (79% of theory) of 2-amino-4-(1-(4-chloro-phenyl)-ethylamino)-6-trifluoromethyl-1,3,5-triazine (racemate) of melting point 99° C.

Starting Materials of the Formula (II)

Example (II-1)

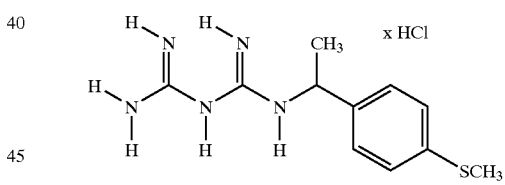

A mixture of 17 g (84 mmol) of 1-(4-methylthio-phenyl)-ethylamine hydrochloride (racemic), 8 g (95 mmol) of dicyandiamide (cyanoguanidine) and 100 ml of 1,2-dichlorobenzene is stirred at 160° C. for 4 hours. After cooling, the resulting crystalline product is isolated by filtration with suction.

This gives 23 g (95% of theory) of 1-[1-(4-methylthio-phenyl)-ethyl]-biguanide hydrochloride (racemate) of melting point 220° C. (decomposition).

It is also possible to carry out the reaction at approximately the same temperature (140° C. to 160° C.) without solvent—i.e. in the melt.

By the method of Example (II-1), it also possible to prepare, for example, the compounds of the formula (II) and their hydrochlorides listed in Table 2 below.

TABLE 2

Examples of compounds of the formula (II) - in all cases, these are the corresponding hydrochlorides!

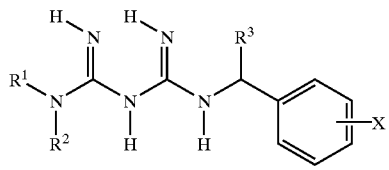

(II)

| Ex. No. | R¹ | R² | R³ | (Position-) X | Physical data and stereochemical specifications |
|---|---|---|---|---|---|
| II-2 | H | H | $CH_3$ | (4-) Cl | (racemate) |
| II-3 | H | H | $CH_3$ | (4-) Cl | (R enantiomer) |
| IIA | H | H | $CH_3$ | (4-) Cl | (S enantiomer) |
| II-5 | H | H | $CH_3$ | (4-) F | (racemate) |
| II-6 | H | H | $CH_3$ | (4-) $OCH_3$ | (racemate) |
| II-7 | H | H | $CH_3$ | (4-) $CH_3$ | (racemate) |
| II-8 | H | H | $CH_3$ | (4-) $CF_3$ | (racemate) |
| II-9 | H | H | $C_2H_5$ | (4-) Cl | (racemate) |
| II-10 | H | $SO_2CH_3$ | $CH_3$ | (4-) Cl | m.p.: 212° C. (racemate) |
| II-11 | H | H | $C_2H_5$ | (4-)Br | (racemate) |
| II-12 | H | H | $C_2H_5$ | (4-) F | (racemate) |
| II-13 | H | H | $C_2H_5$ | (4-)$CH_3$ | (racemate) |
| II-14 | H | H | $C_2H_5$ | (4-) $CF_3$ | (racemate) |
| II-15 | H | H | $C_2H_5$ | (4-) $OCH_3$ | (racemate) |

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of active compound. The amount of water per unit area is advantageously kept constant. The concentration of active compound in the preparation is immaterial, only the application rate of active compound per unit area matters.

After three weeks, the degree of damage to the plants is scored visually in % damage in comparison to the development of the untreated control.

The figures denote:

0%=no effect (like untreated control)

100%=total destruction

In this test, the compounds of Preparation Examples 13, 14, 16, 22, 142, 149, 155, 156, 157, 159 and 160, for example, show strong activity against weeds, and some of them are tolerated well by crop plants, such as, for example, maize, wheat barley and cotton (cf. Table A).

"ai"="active ingredient".

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compounds desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The Figures Denote:

0%=no effect (like untreated control)

100%=total destruction

In this test, the compounds of Preparation Examples 4, 5, 8, 13, 14, 15, 16, 21, 22, 79, 82, 84, 85, 86, 87, 90, 91, 93, 94, 96, 97, 98, 103, 104, 108, 112, 121, 126, 138, 145, 146, 153, 155, 159, 166, 167, 168, 170, 171, 173, 175, 177, 178, 190 and 191, for example, show strong activity against weeds, and some of them are tolerated well by crop plants, such as, for example, wheat and maize (cf. Table B).

TABLE A

Pre-emergence test/greenhouse

| Active compound of Preparation Ex. No. | Application rate (g of ai.(ha) | Maize | Alope- curus | Digi- taria | Echino- chloa | Abu- tilon | Datura | Matri- caria |
|---|---|---|---|---|---|---|---|---|
| (14) structure: Cl-phenyl-CH(CH₃)-NH-triazine(NH₂)-CHF-CH₃ | 500 | 0 | 100 | 100 | 100 | 100 | 100 | 100 |

TABLE A-continued
Pre-emergence test/greenhouse
| Active compound of Preparation Ex. No. | Application rate (g of ai./ha) | Maize | Abut-ilon | Amaran-thus | Sinapis | | | |
|---|---|---|---|---|---|---|---|---|
| 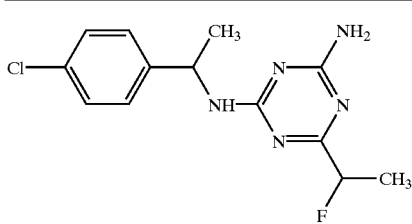 (13) | 1000 | 0 | 100 | 100 | 100 | | | |
| 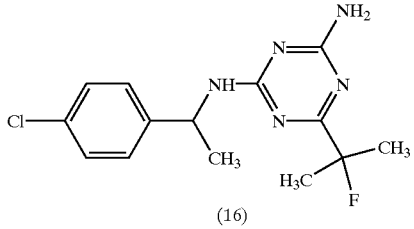 (16) | 1000 | 0 | 80 | 90 | 100 | | | |
| | | Maize | Alope-curus | Setaria | Abut-ilon | Amaran-thus | Galium | Sinapis |
|---|---|---|---|---|---|---|---|---|
| 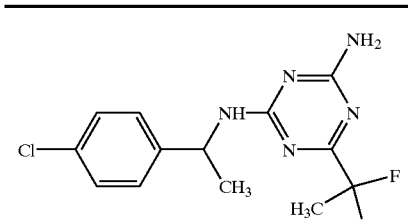 (22) | 1000 | 20 | 100 | 100 | 100 | 100 | 100 | 100 |
| | | Wheat | Cotton | Digi-taria | Echino-chloa | Amaran-thus | Poly-gonum | Vero-nica |
|---|---|---|---|---|---|---|---|---|
| 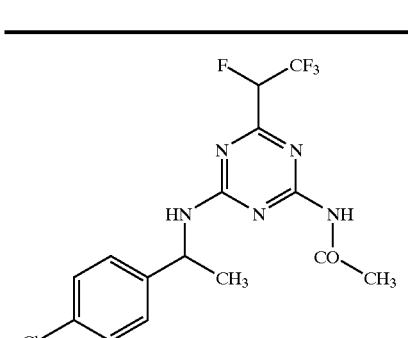 (142) | 500 | 0 | 0 | 80 | 95 | 100 | 100 | 100 |

TABLE A-continued

Pre-emergence test/greenhouse

| Active compound of Preparation Ex. No. | Application rate (g of ai./ha) | Wheat | Cotton | Digitaria | Echinochloa | Polygonum | Solanum | Veronica |
|---|---|---|---|---|---|---|---|---|
| (149) | 500 | 0 | 0 | 95 | 100 | 100 | 100 | 100 |

| | | Wheat | Cotton | Digitaria | Echinochloa | Amaranthus | Solanum | Veronica |
|---|---|---|---|---|---|---|---|---|
| (159) | 1000 | 0 | 0 | 100 | 95 | 100 | 100 | 100 |

| | | Wheat | Cotton | Echinochloa | Setaria | Polygonum | Solanum | Veroinca |
|---|---|---|---|---|---|---|---|---|
| (157) | 500 | 0 | 0 | 100 | 95 | 100 | 100 | 100 |

| | | Wheat | Digitaria | Echinochloa | Setaria | Amaranthus | Polygonum | Solanum | Veronica |
|---|---|---|---|---|---|---|---|---|---|
| (155) | 1000 | 0 | 100 | 100 | 100 | 100 | 100 | 100 | 100 |

TABLE A-continued
Pre-emergence test/greenhouse
| Active compound of Preparation Ex. No. | Application rate (g of ai./ha) | | | | | | | | |
|---|---|---|---|---|---|---|---|---|---|
| 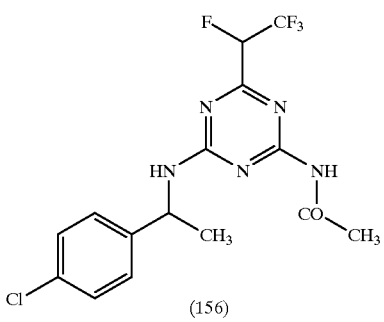 (156) | 1000 | 0 | 100 | 100 | 100 | 100 | 100 | 100 | 100 |
| 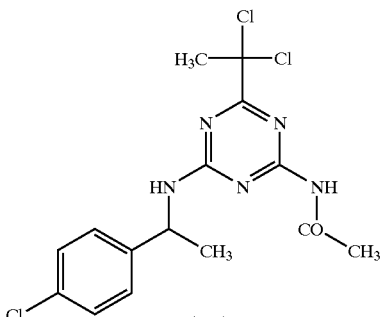 (160) | 1000 | 0 | 100 | 100 | 95 | 100 | 100 | 100 | 100 |
TABLE B
Post-emergence test/greenhouse
| Active compound of Preparation Ex. No. | Application rate (g of ai./ha) | Wheat | Maize | Di-gitaria | Setaria | Cheno-podium | Datura | Poly-gonum | Viola |
|---|---|---|---|---|---|---|---|---|---|
| 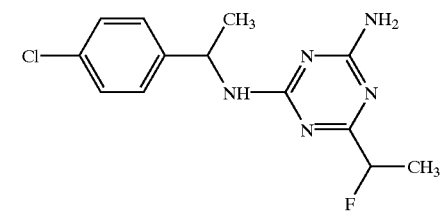 (13) | 125 | 0 | 10 | 80 | 90 | 100 | 100 | 100 | 100 |
| 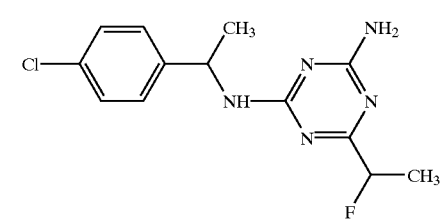 (14) | 125 | — | 20 | — | 80 | 100 | 100 | 100 | 100 |

TABLE B-continued
Post-emergence test/greenhouse
| Active compound of Preparation Ex. No. | Application rate (g of ai./ha) | Maize | Alopecurus | Setaria | Amaranthus |
|---|---|---|---|---|---|
| 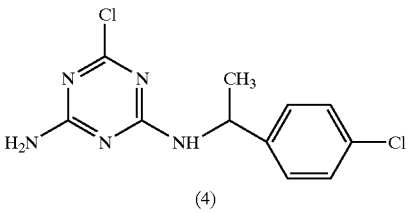 (4) | 1000 | 20 | 80 | 90 | 100 |
| Active compound of Preparation Ex. No. | Application rate (g of ai./ha) | Alopecurus | Avena fatua | Setaria | Abutilon | Amaranthus | Sinapis |
|---|---|---|---|---|---|---|---|
| 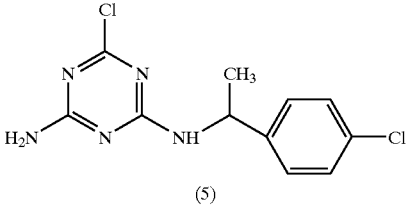 (5) | 1000 | 100 | 100 | 100 | 100 | 100 | 100 |
| 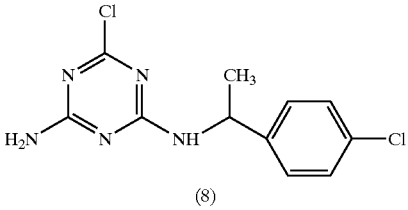 (8) | 1000 | 70 | 80 | 100 | 100 | 100 | 100 |
| 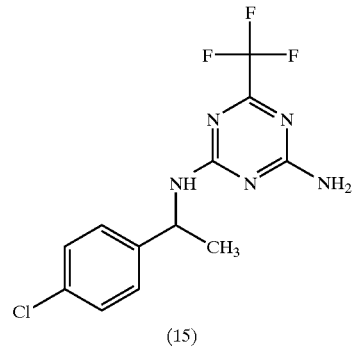 (15) | 1000 | 100 | 100 | 100 | 100 | 100 | 100 |
| 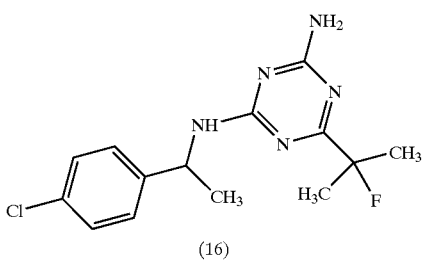 (16) | 1000 | 90 | 95 | 100 | 100 | 100 | 100 |

TABLE B-continued

Post-emergence test/greenhouse

| Active compound of Preparation Ex. No. | Application rate (g of ai./ha) | Avena fatua | Setaria | Abutilon | Amaranthus | Galium | Sinapis | Xanthium |
|---|---|---|---|---|---|---|---|---|
| (21) | 1000 | 70 | 100 | 100 | 100 | 100 | 100 | 100 |
| (22) | 1000 | 100 | 100 | 100 | 100 | 100 | 100 | 100 |

| Active compound of Preparation Ex. No. | Application rate (g of ai./ha) | Wheat | Setaria | Amaranthus | Chenopodium | Polygonum | Viola |
|---|---|---|---|---|---|---|---|
| (108) | 1000 | 0 | 90 | 100 | 100 | 80 | 100 |
| (126) | 500 | 0 | 80 | 100 | 100 | 100 | 100 |

TABLE B-continued
| Post-emergence test/greenhouse | | | | | | | |
|---|---|---|---|---|---|---|---|
| 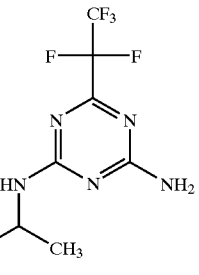 (138) | 250 | 10 | 100 | 100 | 100 | 100 | 100 |
| 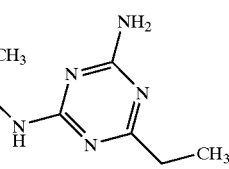 (91) | 250 | 10 | 100 | 100 | 100 | 100 | 100 |
| 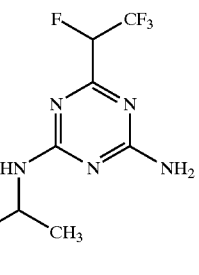 (93) | 250 | 10 | 95 | 100 | 100 | 100 | 100 |
| 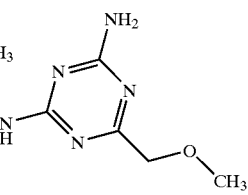 (98) | 250 | 10 | 80 | 100 | 100 | 100 | 100 |
| 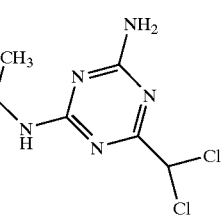 (94) | 250 | 10 | 90 | 100 | 100 | 100 | 100 |

TABLE B-continued

Post-emergence test/greenhouse

| Structure | | | | | | | |
|---|---|---|---|---|---|---|---|
| (96) | 250 | 0 | 80 | 100 | 100 | 100 | 100 |
| (97) | 250 | 10 | 80 | 100 | 100 | 100 | 100 |
| (146) | 250 | 10 | 80 | 100 | 100 | 100 | 95 |
| (153) | 500 | — | 95 | 100 | 100 | 100 | 100 |
| (155) | 250 | 10 | 90 | 100 | 100 | 95 | 95 |

TABLE B-continued

Post-emergence test/greenhouse

| Structure | | | | | | | |
|---|---|---|---|---|---|---|---|
| (157) | 250 | 10 | 80 | 100 | 95 | 95 | 95 |
| (159) | 500 | 10 | 90 | 100 | 100 | 100 | 100 |
| (166) | 500 | — | 100 | 100 | 100 | 100 | 100 |
| (167) | 250 | 10 | 90 | 100 | 100 | 100 | 100 |
| (168) | 500 | 10 | 100 | 100 | 100 | 100 | 100 |

TABLE B-continued
Post-emergence test/greenhouse
| Structure | | | | | | | |
|---|---|---|---|---|---|---|---|
| 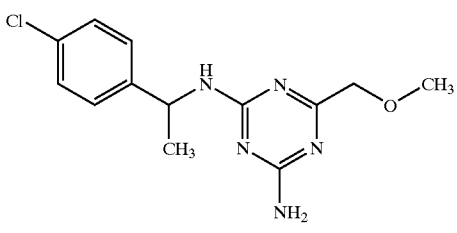 (170) | 250 | 10 | — | 100 | 100 | 100 | 100 |
| 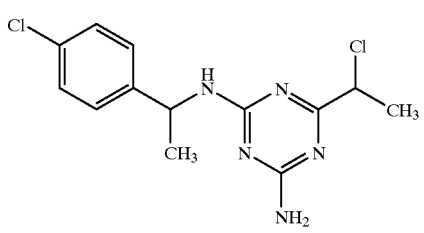 (171) | 250 | 10 | 90 | 100 | 100 | 100 | 100 |
| 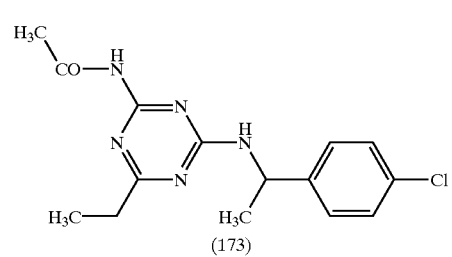 (173) | 500 | 10 | 80 | 100 | 100 | 100 | 100 |
| 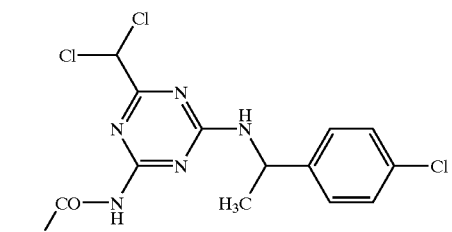 (175) | 500 | 10 | 80 | 100 | 100 | 100 | 100 |
| 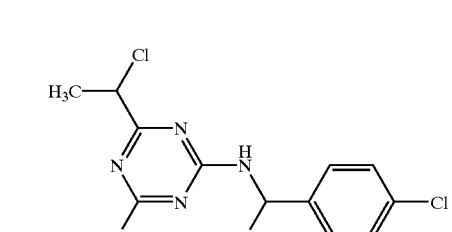 (177) | 500 | 10 | 100 | 100 | 100 | 100 | 100 |

TABLE B-continued

Post-emergence test/greenhouse

| Structure | | | | | | | |
|---|---|---|---|---|---|---|---|
| (178) | 500 | 10 | 70 | 100 | 100 | 100 | 100 |
| (190) | 250 | 10 | — | 100 | 100 | 100 | 95 |
| (85) | 250 | 0 | 95 | 100 | 100 | 100 | 100 |
| (79) | 500 | 0 | 100 | 100 | 100 | 100 | 100 |
| (86) | 1000 | 10 | — | 100 | 100 | 100 | 100 |

TABLE B-continued
Post-emergence test/greenhouse
| | | | | | | | |
|---|---|---|---|---|---|---|---|
| 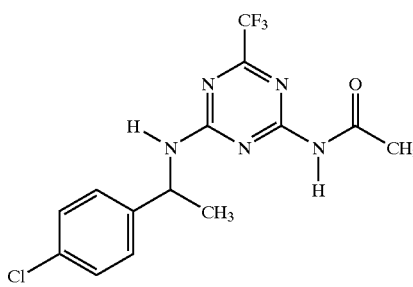 (191) | 500 | 10 | 95 | 100 | 100 | 100 | 100 |
| 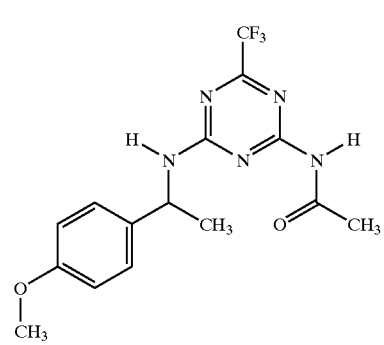 (82) | 500 | 10 | 95 | 100 | 100 | 100 | 100 |
| Active compound of Preparation Ex. No. | Application rate (g of ai./ha) | Wheat | Setaria | Amaranthus | Chenopodium | Stellaria | Viola |
|---|---|---|---|---|---|---|---|
| 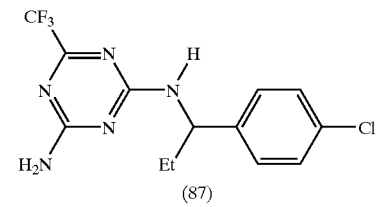 (87) | 250 | 10 | 100 | 100 | 100 | 100 | 100 |
| Active compound of Preparation Ex. No. | Application rate (g of ai./ha) | Maize | Setaria | Amaranthus | Sinapis |
|---|---|---|---|---|---|
| 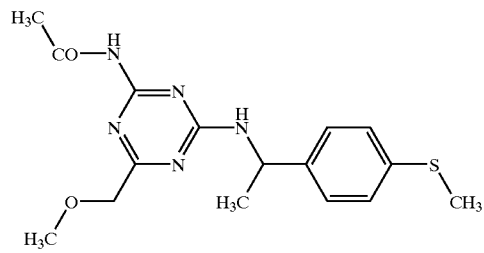 (103) | 1000 | 0 | 100 | 100 | 100 |

TABLE B-continued

Post-emergence test/greenhouse

| Active compound of Preparation Ex. No. | Application rate (g of ai./ha) | Maize | Setaria | Abutilon | Amaranthus | Xanthium |
|---|---|---|---|---|---|---|
| (90) | 1000 | 10 | 100 | 100 | 100 | 90 |

| Active compound of Preparation Ex. No. | Application rate (g of ai./ha) | | Setaria | Amaranthus | Sinapis |
|---|---|---|---|---|---|
| (104) | 1000 | | 100 | 100 | 100 |
| (121) | 1000 | | 100 | 100 | 100 |

| Active compound of Preparation Ex. No. | Application rate (g of ai./ha) | Avena fatua | Setaria | Amaranthus | Galium |
|---|---|---|---|---|---|
| (112) | 500 | — | 90 | 100 | 100 |
| (145) | 1000 | 70 | 100 | 100 | 70 |

TABLE B-continued

Post-emergence test/greenhouse

| Active compound of Preparation Ex. No. | Application rate (g of ai./ha) | Alope-curus | Setaria | Abutilon | Amaranthus | Galium | Xanthium |
|---|---|---|---|---|---|---|---|
| 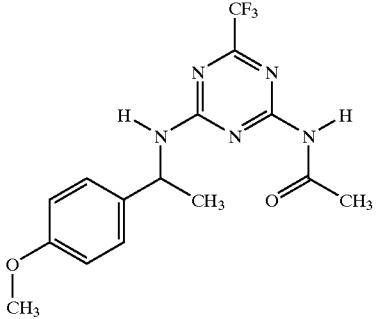 (84) | 1000 | 100 | 100 | 100 | 100 | 100 | 100 |

What is claimed is:

1. A 2,4-diamino-1,3,5-triazine of the formula (I),

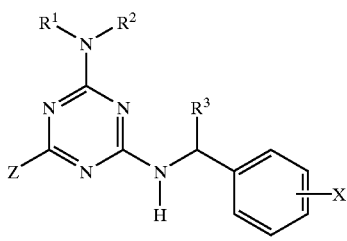

(I)

wherein
- $R^1$ represents hydrogen,
- $R^2$ represents hydrogen or formyl,
- $R^3$ methyl, ethyl, isopropyl or cyclopropyl
- X represents a substituent selected from the group consisting of 2-fluoro, 2-chloro, 2-bromo, 2-methyl, 2-trifluoromethyl, 2-methoxy, 2-difluoromethoxy, 2-trifluoromethoxy, 2-methoxycarbonyl, 2-ethoxycarbonyl, 2-methylthio, 2-methylsulfinyl, 2-methylsulfonyl, 3-fluoro, 3-chloro, 3-bromo, 3-methyl, 3-trifluoromethyl, 3-methoxy, 4-fluoro, 4-chloro, 4-bromo, 4-methyl, 4-ethyl, 4-isopropyl, 4-t-butyl, 4-trifluoromethyl, 4-methoxy, 4-ethoxy, 4-difluoromethoxy, 4-trifluoromethoxy, 4-methoxycarbonyl, 4-ethoxycarbonyl, 4-methylthio, 4-methylsulfinyl, 4-methylsulfonyl, 4-ethylthio, 4-ethylsulfinyl, 4-ethylsulfonyl, 4-trifluoromethylthio, 4-phenyl or 4-phenoxy and
- Z represents a substituent selected from the group consisting of 1-fluoro-ethyl and 1-fluoro-methyl-ethyl.

2. A herbicidal composition comprising one or more compounds of the formula (I) according to claim 1 and one or more extenders and/or surfactants.

3. A method for controlling weeds, comprising the step of allowing an effective amount of a compound of the formula (I) according to claim 4 to act on weeds or their habitat.

4. A 2,4-diamino-1,3,5-triazine of the formula (I),

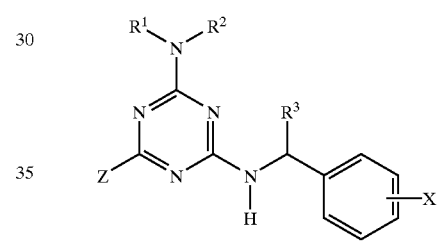

(I)

wherein
- $R^1$ represents hydrogen,
- $R^2$ represents hydrogen,
- $R^3$ methyl or cyclopropyl,
- X represents a substituent selected from the group consisting of 4-trifluoromethoxy, 4-chloro, 3-bromo, 4-bromo and 3-fluoro,
- Z represents 1-fluoro-ethyl or 1-fluoro-methyl-ethyl.

5. A herbicidal composition, comprising one or more compounds of the formula (I) according to claim 4 and one or more extenders and/or surfactants.

6. A method for controlling weeds, comprising the step of allowing an effective amount of a compound of the formula (I) according to claim 5 to act on weeds or their habitat.

* * * * *